United States Patent [19]

Gess et al.

[11] Patent Number: 5,340,442

[45] Date of Patent: Aug. 23, 1994

[54] EVALUATING FURNISH BEHAVIOR

[75] Inventors: Jerome M. Gess, Bellevue; Dennis E. Petersen, Puyallup; Terry N. Adams, Tacoma; Russell J. Martz, Puyallup, all of Wash.

[73] Assignee: Weyerhaeuser Company, Tacoma, Wash.

[21] Appl. No.: 765,906

[22] Filed: Sep. 24, 1991

[51] Int. Cl.$^5$ .......................................... G01N 11/00
[52] U.S. Cl. ...................................... 162/198; 162/49
[58] Field of Search ................. 162/49, 198; 73/53.04, 73/53.05; 416/231 A

[56] References Cited

U.S. PATENT DOCUMENTS

| | | | |
|---|---|---|---|
| 2,734,378 | 2/1956 | Meyers | 73/63 |
| 3,402,897 | 9/1968 | Willems | 416/231 A |
| 3,585,106 | 6/1971 | Sepall et al. | |
| 3,630,636 | 12/1971 | Hill | 416/231 A |
| 3,724,957 | 4/1973 | Tamate et al. | 162/198 |
| 4,024,754 | 5/1977 | Alfthan | 73/63 |
| 4,613,406 | 9/1986 | Gess | 162/49 |
| 4,662,991 | 5/1987 | Kärnä et al. | 162/198 |
| 4,708,011 | 11/1987 | Rautakorpi et al. | 73/63 |
| 4,891,098 | 1/1990 | Renjilian et al. | 162/198 |
| 4,969,351 | 11/1990 | Halley et al. | 73/63 |
| 5,026,455 | 6/1991 | Lehtikoki et al. | 73/53.03 |
| 5,090,816 | 2/1992 | Socha | 416/231 A |

FOREIGN PATENT DOCUMENTS

WO91/0600  5/1991  PCT Int'l Appl.

OTHER PUBLICATIONS

Patent Abstracts of Japan, vol. 10, Sep., 1986 & Japanese patent A 61-104257.
PCT International Search Report dated Feb. 2, 1993 for International Application No. PCT/US 92/08116.
Gess, Proceedings, Tappi Papermaking Conference, Portland, Oreg., 185-189 (1983).
Gess, Notes, Tappi Retention and Drainage Seminar, 77-81 (1983).
Gess, Tappi, Advanced Topics in Wet End Chemistry Short Course, Memphis, Tenn. (1987).
Gess, Tappi, Retention and Drainage Short Course, 49-52 (1989).
Gess, Preprints, Tappi Annual Meeting, A27-A32 (1989).

*Primary Examiner*—W. Gary Jones
*Assistant Examiner*—Brenda Lamb
*Attorney, Agent, or Firm*—Klarquist Sparkman Campbell Leigh & Whinston

[57] ABSTRACT

A drainage tester evaluates the reaction pattern of one or more reactions in a paper pulp furnish to predict behavior of the pulp on a paper line. The tester includes a mixing container in which an additive is mixed with the slurry under conditions that prolong the reactions in the container such that they take longer than the same reactions on a paper line. The mixer can also mimic the kinetic conditions (such as mixing by turbulence or passive diffusion) under which the additive is mixed with the furnish on the paper line. A test container has a screen bottom that separates furnish solid from slurry water by developing a pressure differential across the screen. An intermediate container is positioned between the mixing container and test container to provide a constant hydrostatic head on furnish transferred to the test container. A sensor above the screen in the test container monitors changes in the optical characteristics of a sheet formed on the screen to automatically determine the drainage time of the formed sheet. Sequential equal volume aliquots of furnish are withdrawn from the mixing container and sent to the test container at preselected time intervals after chemical additives are mixed with the furnish in the mixing container. Physical characteristics of the sheet, such as fines retention, drainage time and visual appearance, are recorded as a function of time from addition of additive to the mixing container. Behavior of the sheet on the paper line can be predicted in this manner to help an operator efficiently operate a paper machine system.

22 Claims, 18 Drawing Sheets

Pipe

Effect of Cation/Anion Retention Aid System on Retention
(Fiber+Calcium Carbonate)

Effect of Cation/Anion Retention Aid System on Pigment Retention
(Fiber+Calcium Carbonate)

FIG. 24 Effect of Cation/Anion Retention Aid System on Pigment Retention (Fiber+Calcium Carbonate)
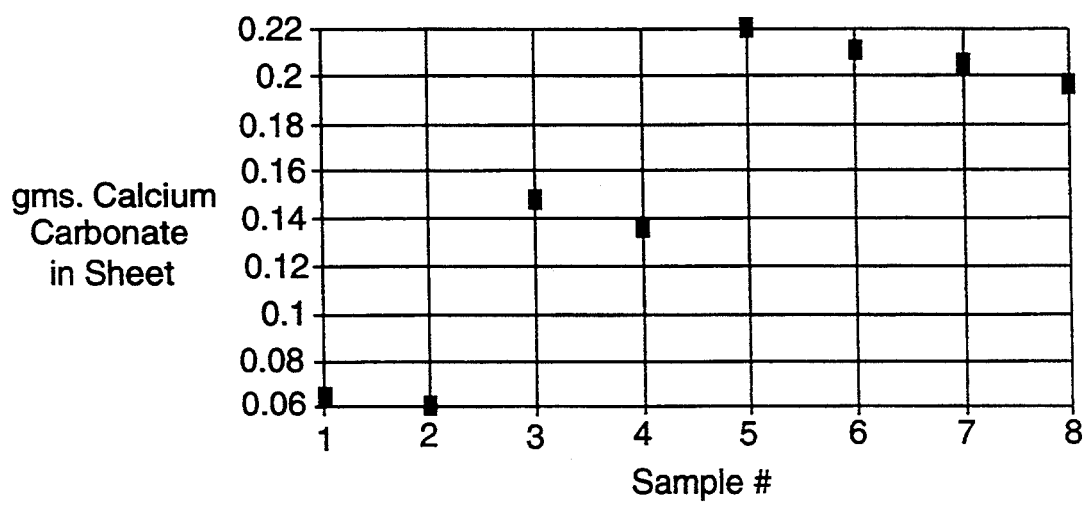
FIG. 25 Effect of Cation/Anion Retention Aid System on Fiber Retention (Fiber+Calcium Carbonate)
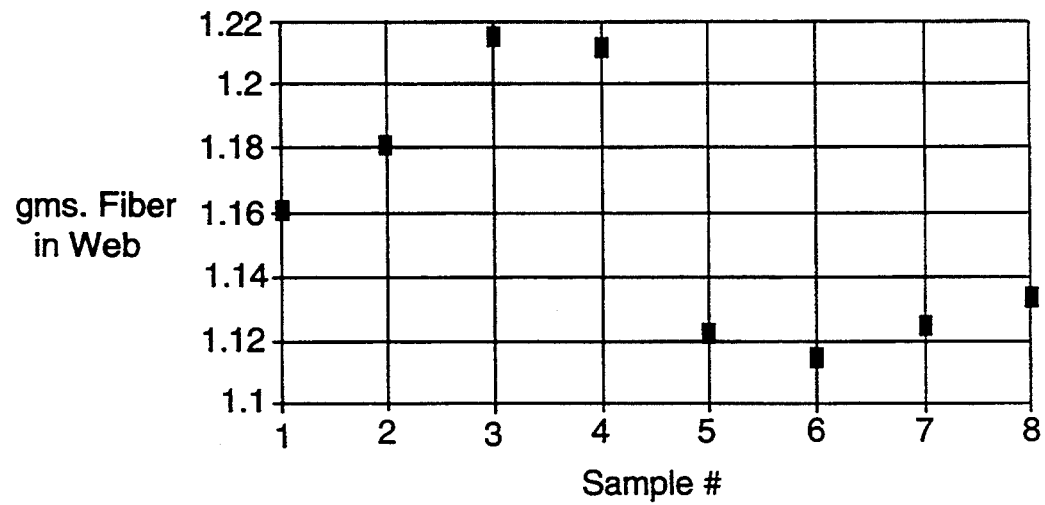

EVALUATING FURNISH BEHAVIOR

BACKGROUND OF THE INVENTION

1. Field of the Invention

The present invention concerns a method and device for evaluating the behavior of a given papermaking furnish in response to addition of chemical additives.

2. General Discussion of the Background

Paper makers have several simple methods and devices for predicting behavior of pulp on a paper machine. An example of such a method is estimating the drainage time of a papermaking stock. The drainage time can be estimated by the TAPPI Standard Drain Time, which requires placing a standardized sample of the stock in a small laboratory sheet mold and visually estimating the elapsed time until sheet formation after a drain valve is opened. The values so obtained may or may not correlate well with the performance of the same stock at the paper machine wet end depending on such variables as the pattern of chemical addition. Visual estimations of drainage time alone are subjective and only marginally capable of standardization.

A more sophisticated method for measuring the drainage characteristics of a papermaking stock is described in U.S. Pat. No. 4,613,406 to Gess. In this patent, a slurry on a screen is dewatered in a sheet mold using vacuum under a screen. The pressure differential across the screen is measured as a function of time as the sheet forms on the screen. When the data so obtained are plotted, the resulting curve shows four generally linear sections of different slopes. The first inflection point that occurs between the first two linear curves marks the transition point at which a random collection of fibers form a web as the stock is dewatered. This first inflection point is believed to correlate with the "wet line" on the forming section, which is the appearance of a flat, wet surface on the web. The second inflection point, which occurs between the second and third linear sections of the curve, indicates where the vacuum no longer compacts the web. This second inflection point is believed to correspond closely to the "dry line" on a forming section, which is the appearance of a dry surface on the web. Finally, a third inflection point occurs between the third and fourth linear portions of the curve, and indicates where the initial dewatering is essentially complete and air is first drawn completely through the web. The apparatus and method disclosed by Gess is described in *Proceedings*, TAPPI Papermaking Conference, Portland, Oreg., 185–189 (1983) and Notes, TAPPI Retention and Drainage Seminar, 75–81 (1983).

Additional information about the process of the Gess patent is provided by Gess in TAPPI, *Advanced Topics in Wet End Chemistry Short Course*, Memphis, Tenn. (1987). That paper analyzes a curve of sheet weight versus drainage time and discusses how this relationship predicts fines sensitivity of the forming system. The curve has two linear portions of differing slopes. The first linear portion of the plot is apparently related to the forming wire. In this portion of the plot, reaction is controlled by the pore size of the forming fabric, and the fines in the system pass through the pores of the forming fabric. The second linear portion is believed to reflect the fines retention characteristics of the sheet itself. The relationships between increasing sheet weight and drainage time are further analyzed by the same author in two more recent papers: TAPPI, *Retention and Drainage Short Course*, 49–52 (1989) and *Preprints*, TAPPI Annual Meeting, A27–A32 (1989).

A practical device that uses this relationship to predict performance of a stock on the forming section of a paper machine is described in U.S. Pat. No. 4,969,351. Sequential samples of furnish from a container are supplied to a sheet mold that automatically measures drainage time of each sheet formed from the furnish. The volume of each sequential sample of furnish is incremental such that a linear plot of drainage time versus increasing basis weight of the forming sheet is obtained. These representative data points allow an operator to predict drainage time of a sheet having any basis weight within the linear range of the data. The disclosed apparatus rapidly forms a series of sheets of differing basis weights to give the operator a timely indication of factors, such as white water fines buildup, that can affect operation of the forming section.

The device shown in U.S. Pat. No. 4,969,351 is unable, however, to monitor progress of physical or chemical changes in the slurry over time. The sequential aliquots of slurry must have uniform physical and chemical characteristics (be in equilibrium) for the linear plot of increasing basis weight accurately to predict drainage time. Hence, the properties of the slurry cannot be varied, and the sequential aliquots must be of different volumes.

Other patents have disclosed devices for determining the behavior of fiber pulp. U.S. Pat. No. 4,708,011, for example, weighs sequential pulp cakes on a wire screen and measures the pressure differential and volume of air flowing through the cake. U.S. Pat. No. 4,024,754 measures the rate of flow of a liquid forced under pressure through wood fiber pulp to assess the drainability of the material. Finally, U.S. Pat. No. 2,734,378 tests the filterability of a pulp mat on a screen by flowing water through the mat. In this patent, pulp is obtained at timed intervals from the refining end of a stock system and tested for filterability to provide an instantaneous running record of pulp freeness.

None of the aforementioned methods is able, however, to follow the effect of chemical additions of the elements of a papermaking furnish as a function of the time and mode of mixing the chemicals with the furnish. Prior systems also fail to provide a test system in which the reaction conditions of the test system mimic the kinetic conditions under which an additive is mixed with a pulp slurry in a papermaking line. Competing considerations of the free energy of reactants and collision kinetics are not addressed by the prior art systems that merely focus on the behavior of pulp at a specific point in time. Finally, some prior systems have the drawback of changing the physical and chemical characteristics of pulp slurry by unintentionally mixing the slurry with centrifugal pumps that transport the slurry within a test system.

It is therefore an object of the present invention to provide an improved method for evaluating a chemical reaction in a paper pulp furnish that accurately predicts behavior of the pulp on and in a paper machine system.

Another object of the present invention is to provide an improved device that follows the effect of chemical additives as a function of mixing time on a papermaking furnish to help select process parameters for producing cellulosic sheets from the slurry.

Another object is to provide such a method and device that can help evaluate competing reaction kinetics, such as the effects of the free energies of the products that can be formed versus the collision kinetics of a reaction.

Yet another object is to provide an improved tester that more accurately reproduces the kinetic conditions under which additives react with the slurry in a paper making machine, and can help choose preferred kinetic conditions for the reaction.

Finally, it is an object of the invention to provide an improved tester that transports slurry through the test system without substantially affecting the reaction kinetics in the pulp.

These and other objects of the invention will be understood more clearly by reference to the following description and drawings.

SUMMARY OF THE INVENTION

The present invention is a method and device for evaluating the pattern of one or more reactions in a paper pulp furnish to predict behavior of the pulp on a paper line. The device includes a holding or mixing container having an agitator that mixes additives with furnish and maintains a uniform suspension throughout the container. The agitator can be used to mimic the kinetic conditions under which an additive is mixed with the furnish on the paper line. Agitation of the furnish also ensures uniformity of collision reaction kinetics between the furnish and additives throughout the container.

The device also includes a separate test container having a screen bottom that separates furnish solids from slurry water. An intermediate container between the holding and test containers maintains a constant head on a sample of the furnish in the intermediate container to ensure that a constant volume of furnish is transferred through lines from the holding container to the test container. A suction generator dewaters the furnish in the test container to form a sheet by subjecting the furnish to a pressure differential created by reducing pressure beneath the test container screen. A timer measures the time elapsed between initially mixing the additives with the furnish, and removing the furnish from the mixing container.

A separate sensor detects changes in the optical characteristics of a sheet that forms on the screen as the slurry is dewatered. The sheet drainage time, and other variables of interest, are expressed as a function of the amount of time that elapsed since additives were mixed with the furnish. The relationship between elapsed time and the drainage time or other variable of interest allows an operator to prepare a family of curves comparing the progress of different additive reactions in the furnish. The temporal relationships between such factors as pigment retention, fines retention, and drainage time can be studied. The effect of turbulent or non-turbulent introduction of additives into a paper line can be monitored, and pulp behavior can be optimized by choosing the mode of addition that provides a contemporaneous increase in such behaviors as pigment and fines retention. Alternatively, pulp behavior can be evaluated by introducing into the pulp slurry different amounts of additives, such as retention aids. The interrelationship between the amount of additive and the mode of mixing provides important information that can be used to optimize sheet retention on a paper line.

The present invention also includes a method for evaluating a reaction in a paper pulp by combining the furnish with an additive in the mixing container under conditions that prolong reactions such that they require longer to complete in the container than on the paper line. Container reactions are prolonged, for example, to take thirty to sixty minutes by mixing additives with the slurry under conditions of minimum turbulence that still maintain uniformity of the suspension in the container. These same reactions may take only a few seconds or minutes to occur on a paper line. Minimum turbulent mixing with uniform suspensions is achieved, for example, by agitating the mixture in the container with a mixing blade at 1–100 RPM. The mixing blade is preferably configured to provide uniform reaction kinetics throughout the container by recirculating the pulp toward the top of the container.

The mixing conditions in the container can also be varied to mimic the kinetic conditions under which additives are supplied to the pulp on the paper line. Low speed mixing (for example, 10 RPM rotation of the mixing blade) is used to evaluate reaction rates in low turbulence, diffusion limited additions to paper lines. Higher speed mixing (for example, 100 RPM rotation of the mixing blade) corresponds to reaction rates on paper lines where additives are added to the line under turbulent mixing conditions. By varying the speed of the mixing blade, one can study the effect of different modes of introducing additives to the line.

After addition of the chemical additives to the pulp in the mixing container, equal volume samples of the furnish are then transferred at preselected intervals from the holding container to the test container. Each furnish sample is dewatered to form a sheet by subjecting the furnish to a pressure differential. Several characteristics of the forming or formed sheet are measured to determine the effect of additive introduction as a function of time since the additive was provided to the mixture. The drainage time of each sample, for example, is automatically determined as each sheet forms, and is correlated with the amount of time that elapsed between initially reacting the additive with the furnish and removing the furnish from the mixing container. As previously mentioned, other important relationships can also be studied, including pigment retention, fines and fiber retention, amount of retention aid added, freeness, turbulent versus passive mixing, and visual appearance of the formed sheet.

In preferred embodiments, the furnish is mixed with the additive under turbulent conditions. These turbulent conditions can be induced by a horizontally rotating mixing blade having a pair of oppositely inclined faces that direct a portion of the furnish upward while the blade rotates. This mixing blade assures that the reaction between the furnish and additive proceeds uniformly throughout the sample until the sample is removed from the mixing container. Peristaltic pumps convey the furnish between the different containers to avoid altering the reaction kinetics of the slurry while it is being transported.

BRIEF DESCRIPTION OF THE DRAWINGS

FIG. 24 is a graph similar to FIG. 23 showing the effect on pigment retention.

FIG. 25 is a graph similar to FIG. 24 showing the effect on fiber retention.

DETAILED DESCRIPTION OF PREFERRED EMBODIMENTS

Figure 1:
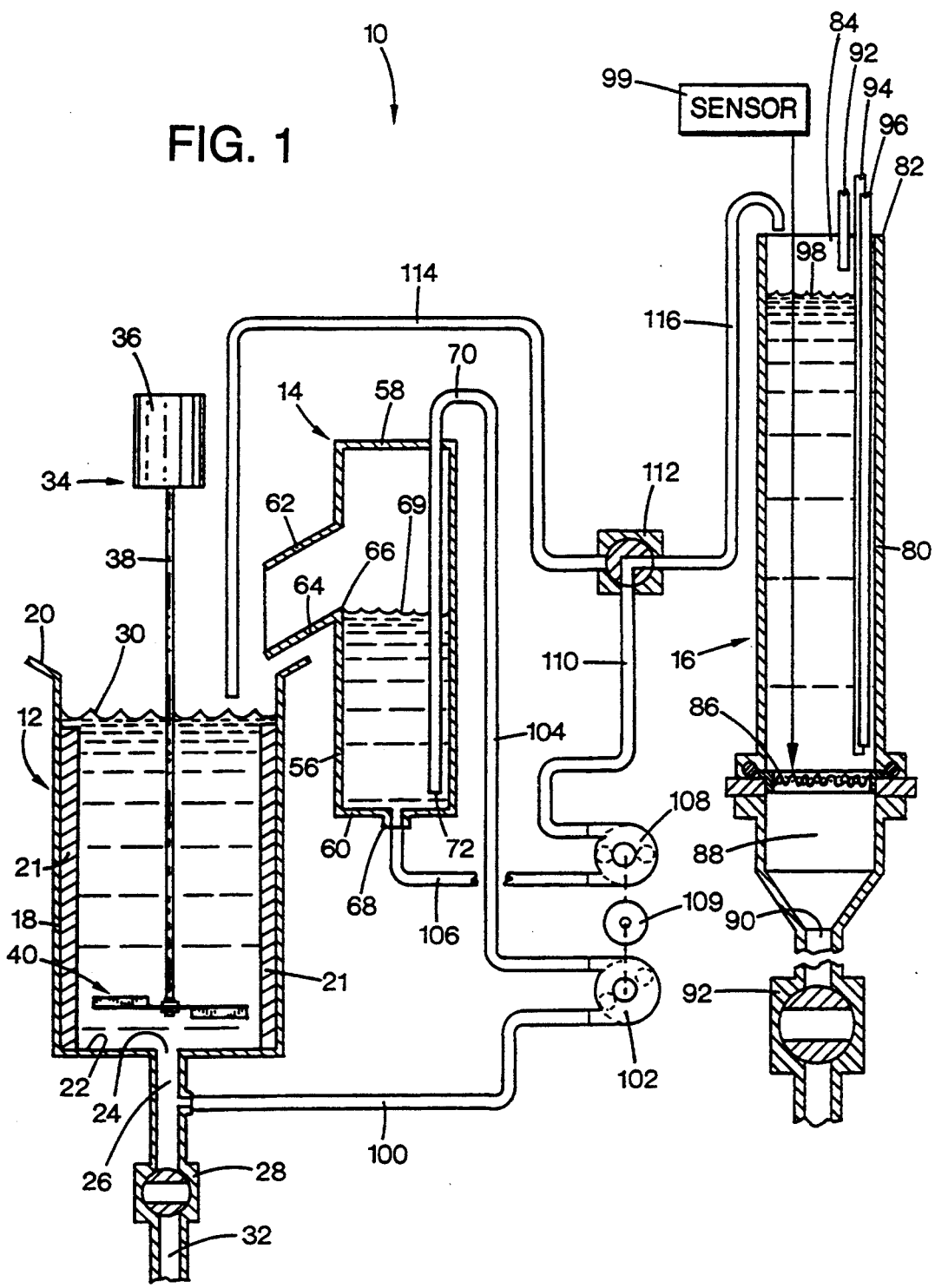
FIG. 1 is a partially schematic, cross-sectional view of the evaluation instrument of the present invention.

The construction and operation of the apparatus of the present invention, and the method of its use, can best be understood by reference to the drawings and the following detailed description of several preferred embodiments. One embodiment of the drainage tester 10 is shown in FIG. 1 to include a holding container 12, an intermediate container 14, and a test container 16. The holding container 12 includes a cylindrical sidewall 18 having an open top circumscribed by an annular inclined lip 20. A pair of opposing, flat vertical vanes or fins 21 project inwardly from sidewall 18. The bottom of holding container 12 is defined by a flat bottom face 22 having a central drain 24 that communicates with a drain line 26. Drain line 26 in turn communicates with a drain valve 28, which can be moved between the closed position (shown in FIG. 1) and an open position in which the pulp furnish 30 in holding container 12 is drained through an outlet 32 for removal from the system.

Holding container 12 includes a mixer 34 for efficiently and thoroughly mixing a chemical additive with the furnish 30 in container 12. The mixer 34 produces a uniform pulp suspension with minimal turbulence that slows reactions which occur very quickly on a paper line. Mixer 34 can also provide kinetic conditions in container 12 that mimic the kinetic conditions of reacting the additive with the furnish on a paper line. FIG. 1 shows that mixer 34 includes a variable speed motor 36 suspended above the open top of container 12. Motor 36 drives a rotary shaft 38 that extends from motor 36 through the surface of furnish 30 and toward bottom wall 22.

Figure 2:
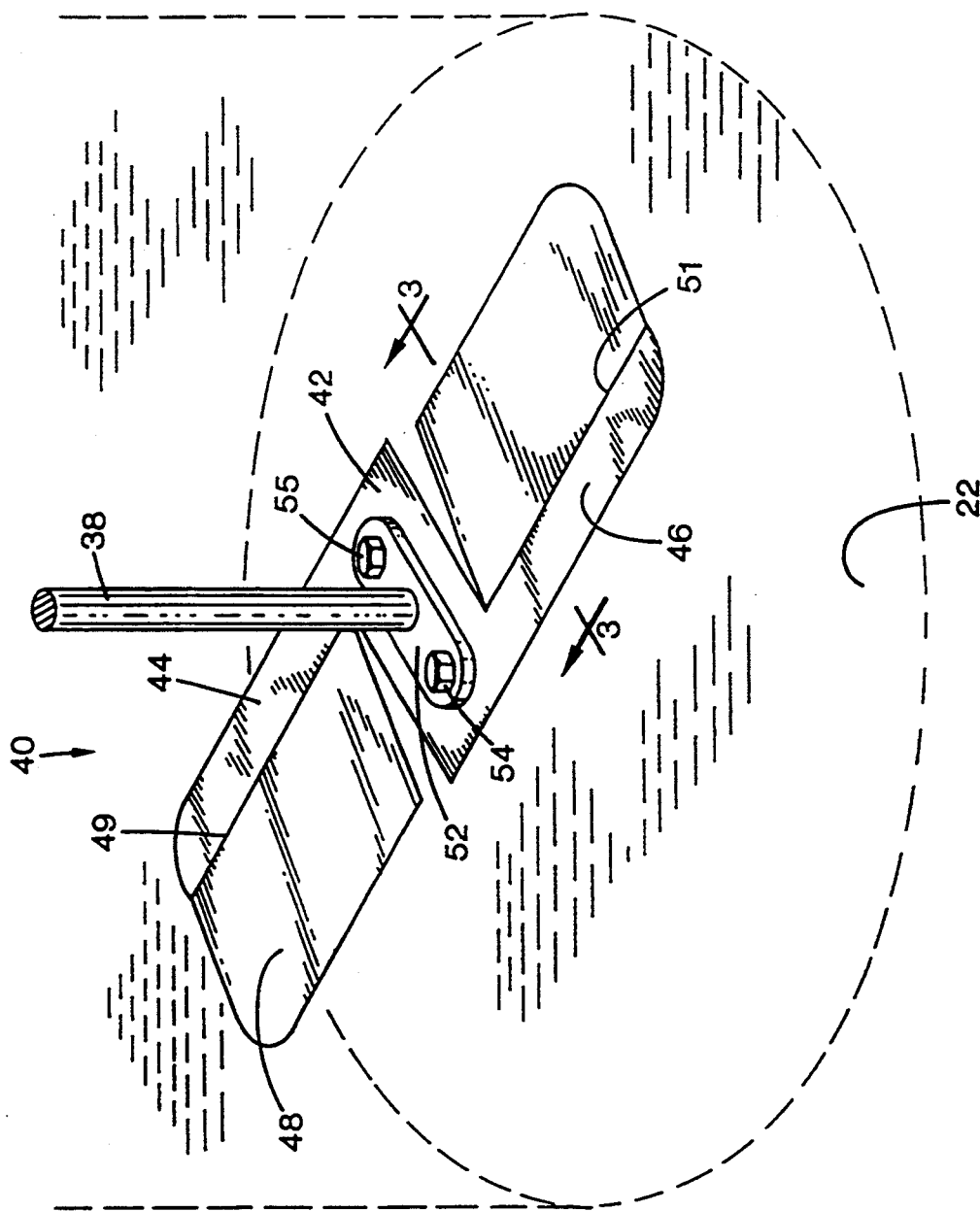
FIG. 2 is an enlarged perspective view of the mixing blade of the present invention, the mixing container body being shown in phantom.
Figure 3:
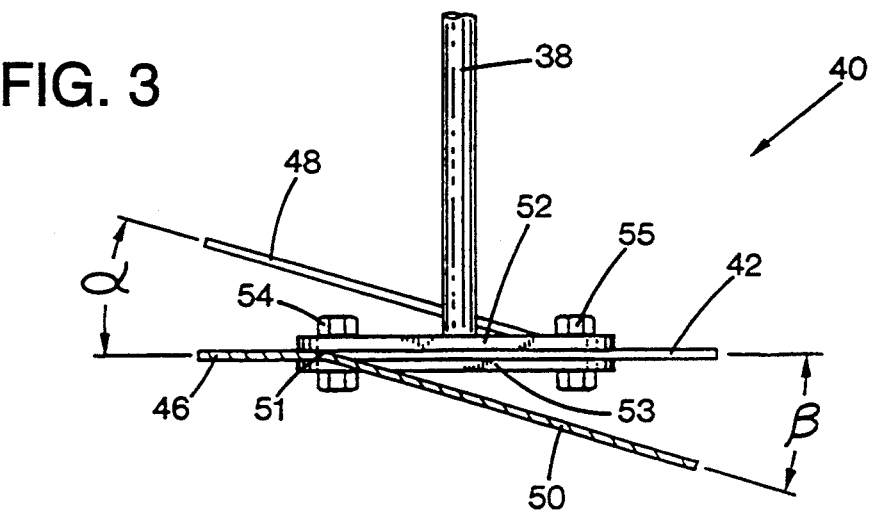
FIG. 3 is a cross-sectional view of the mixer blade taken along view lines 3—3 of FIG. 2.

At the free end of shaft 38 is a mixing blade 40, that is shown in greater detail in FIGS. 2 and 3. The blade includes a horizontal, rectangular central plate 42 having first and second arms 44, 46 that are co-planar with central plate 42 and extend in opposite directions from one another parallel to bottom surface 22 of container 12. A rectangular, flat face 48 inclines upwardly from an inner edge 49 of arm 44, extending at an angle $\alpha$ (FIG. 3) of fourteen degrees to the plane of arms 44–46. A corresponding rectangular, flat face 50 inclines downwardly from an inner edge 51 of arm 46, and extends below the plane of arms 44–46 at an angle $\delta$ of about fourteen degrees. The angles $\alpha$ and $\delta$ preferably range from thirteen to fifteen degrees. Shaft 38 is secured to central plate 42 by a pair of flanges 52, 53 that fit flush against top and bottom faces of plate 42. Flanges 52, 53 are secured in place by bolts 54, 55. Shaft 38 can alternatively be secured to plate 42 by mating threads on the shaft and plate.

The intermediate container 14 has a cylindrical body 56, flat top and bottom walls 58, 60 and a rectangular cross-section side arm 62 that includes a sloping bottom surface 64. The surface 64 intersects the sidewall 56 along a level line 66. Surface 64 is parallel to a plane through annular lip 20 and extends above the lip toward the interior of container 12. An open face of arm 62 opens over container 12 such that liquid flows downhill along sloping surface 64 and into the open top of container 12.

A drain 68 extends through the bottom wall 60 of container 14, and provides an outlet through which furnish 69 in the container can be removed. A recycle line 70 extends through the top wall 58 of container 14 and terminates at an open end 72 near bottom 60. The hydrostatic head of the furnish 69 in container 14 is maintained at a constant pressure by keeping the depth of the furnish in that container constant. Once a preselected depth is exceeded, the furnish flows over level line 66 back into container 12. The constant hydrostatic head on furnish 69 allows equal volumes of furnish to be withdrawn from intermediate container 14 and sent to test container 16 where a sheet is formed and its drainage characteristics assessed.

Test container 16 includes a tall cylinder 80 having an open top 82, internal test chamber 84 and a bottom screen 86 for separating furnish solids from slurry water. Below screen 86 is a suction generating chamber 88 that communicates with a drain line 90. A valve 92 is interposed in drain line 90, and can move between the closed position shown in FIG. 1 (in which furnish does not exit chamber 88) and an open position in which furnish can freely exit chamber 88 through drain line 90.

Three level probes 92, 94, 96 are located in test container 16 to monitor the depth of furnish 98 in the container. An optical sensor 99 is positioned above the open top 82 of container 16 and directs a beam of light toward screen 86 to determine the optical characteristics of a sheet forming on the screen. The sensor 99 can be, for example, product model no. WL20 from Sick Optik of Germany. Probe 92 is a start probe that terminates near the open top 82 and begins measuring the drainage time when the level of furnish 98 falls below the distal tip of the probe. Probe 96 is a hold off probe that inhibits operation of optical sensor 99 until the level of furnish 98 falls below the distal tip of probe 96. The probe 94 is a reference probe for the circuit.

Furnish in drainage tester 10 is conveyed through the testing system by a series of rigid transfer lines that convey furnish without significantly affecting the kinetics of any reactions that are occurring in the furnish. The lines are sufficiently rigid to inhibit ballooning of the lines in response to elevated internal pressure. The lines may be neoprene tubing obtained from Cole Parmer of Chicago, Ill., under product no. MT-6404-18. Transfer line 100 communicates with drain line 26 below container 12 and conveys furnish that is drawn by peristaltic pump 102 into line 104. Line 104 communicates with recycle line 70 such that furnish from holding container 12 can be conveyed into intermediate container 14. A drain line 106 communicates with drain 68 in the bottom of intermediate container 14. Line 106 in turn communicates with a peristaltic pump 108 that draws furnish out of intermediate container 14 and moves the furnish into line 110 that communicates with a directional valve 112.

The position of valve 112 determines whether stock is recirculated through a recirculation line 114 or is transferred through line 116 to test container 16. When the valve is in the position shown in FIG. 1, furnish flows into test container 16. Between tests, however, valve 112 is moved to an alternate position in which furnish constantly recirculates from container 14 to container 12. Both peristaltic pumps 102, 108 are driven by a common motor 109. The pumps may be obtained from Cole Parmer under part nos. MT-7553-20 and MT-7018-21.

In operation, holding container 12 is filled with furnish 30. An additive or additives are mixed into the furnish at a recorded time by introducing a known quantity of the additive through the open top of container 12. Motor 36 is preferably energized prior to introducing the additive such that blade 40 rotates in a horizontal plane and preferably mixes the additive or additives with the furnish from the time of their addition. The RPM of blade 40 can be altered by changing the speed of variable speed motor 36, thereby providing poor mixing (for example, 10-30 RPM, preferably 10 RPM) or good mixing (for example, 70-100 RPM, preferably 100 RPM). Poor mixing approximates addition to a paper line under conditions that mimic primarily diffusion controlled distribution of the additive through the pulp. Good mixing more closely approximates introduction of additives to a paper line under conditions that mimic primarily turbulent mixing of the additive and pulp on a paper line.

With drain valve 28 closed, pump 102 draws furnish through drain line 26 and line 100 into line 104 and thence to container 14. The furnish in container 14 rises to a level even with line 66, at which time the furnish flows over line 66 down inclined surface 64 and back into holding container 12. In this manner, the level of furnish 69 in container 14 is maintained constant to provide a uniform hydrostatic head that ensures that the quantity of furnish removed from the intermediate container 14 is constant. Furnish is preferably constantly recirculated between containers 12 and 14 to assist in maintaining a uniform suspension in container 12. Pulp slurry is drawn from the bottom of container 12 and introduced through arm 62 back into the open top of container 12, thereby assuring uniform distribution of additives throughout the pulp.

Furnish 69 is removed from container 14 by activating pump 108, at a preselected time before or after introduction of additives into container 12, to withdraw a constant volume of furnish through line 106 and into lines 110, 116. The known, constant volume of furnish is then emptied through open top 82 into test container 16. A constant volume vacuum is then developed in chamber 88 by a suction pump (not shown), with drain valve 92 open. Furnish is then drained through screen 86 into chamber 88 and out of drain 90. The screen separates fibers from the pulp furnish slurry and retains a pulp mat of the furnish on the screen. The screen is designed substantially to duplicate the filtering or dewatering apparatus on a paper machine forming wire. The constant applied vacuum exerts a negative pressure differential on the sample held on the screen.

The drainage time of a given sample is determined, as the sheet forms, in the manner described in U.S. Pat. No. 4,969,351 which is incorporated by reference. Several other characteristics of each sheet can also be determined by tilting container 16 away from screen 86 and removing the formed sheet from the screen. Other tests can then be performed on the sheet to determine the patterns of reaction in the pulp. Examples of other sheet characteristics that can be determined include (without limitation) pigment retention, fines retention, fiber retention, and the appearance of the sheet. Fines and fiber retention can be calculated by assuming that the solids content of the sheet consists of pigment, fines and fiber. Hence, the fines and fiber weight is the weight of the sheet minus the weight of pigment present. The appearance of the sheet can be rated either by an automated scanner or subjectively by an evaluator who visually rates the appearance of the formed sheet.

Plots of Drainage Time Versus Vacuum

Figure 4:
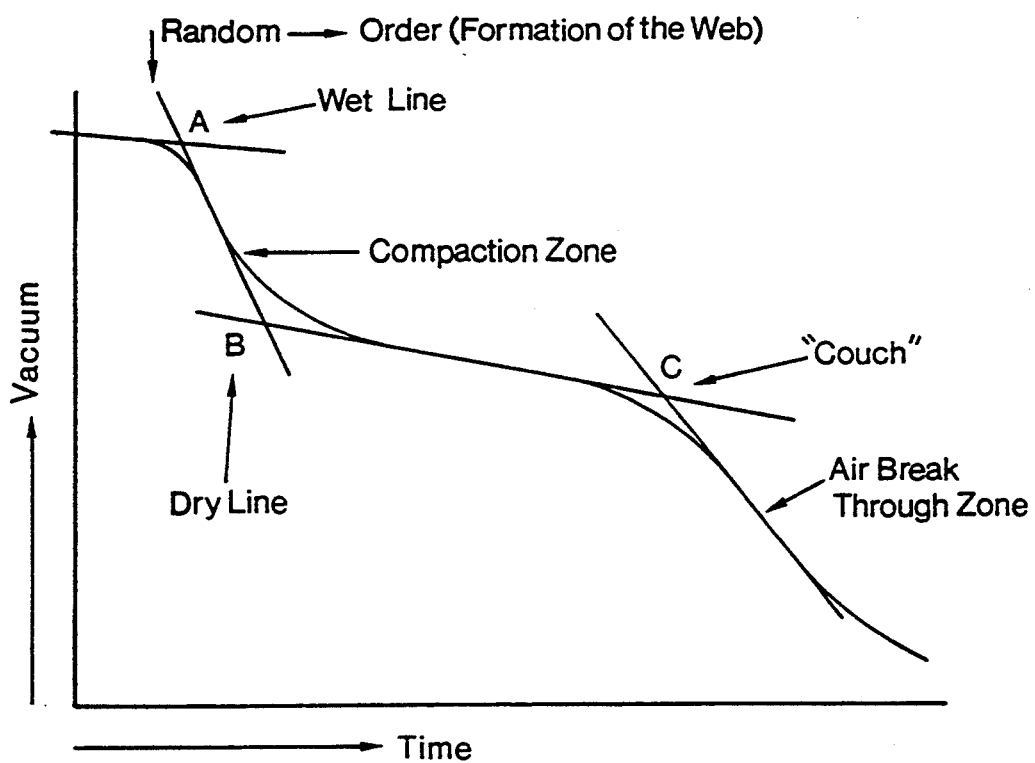
FIG. 4 is a recording of pressure differential across a forming sheet on a screen, as a function of time, obtained by a prior apparatus.

When the drainage test is performed, a plot of drainage time versus vacuum shows three distinctive points of inflection, labeled A, B and C in FIG. 4. Each of these points can be correlated with characteristics of the mat being formed, and the drainage time until each of the points can be used to assess the progress of chemical reactions in a slurry sample being studied. The high initial vacuum exerted on the pad continues to a point of inflection A where there is a significant drop in vacuum. This "A break" represents formation of the pad and drainage through it, including some compression of the web by water surface tension forces, until air begins to be pulled through the pad. This first phase of drainage terminates when the fibers have formed a web, and this termination roughly correlates with the appearance of the wet line on the pulp running on the wire of the paper machine.

From points A to B on the FIG. 4 tracing, further free water is removed. During this second phase of the drainage process, the web is compacted by vacuum forces. This compaction occurs as water is removed by the decrease in the void volume of the web under the influence of vacuum forces. This portion of the drainage process ends with the appearance of the second point of inflection, break point B on the FIG. 4 tracing. The B break apparently correlates with the appearance of the dry line on the paper machine. In this zone of the paper machine, water removal is accomplished primarily by vacuum, typically flat vacuum boxes. The forces in the A–B zone are stronger than the mild forming forces, such as gravity and forming table foil vacuum forces, that preceded the A break. The B break can be automatically determined by an optical detection that shines a beam of light at the forming sheet and measures the intensity of a reflected beam. The beam reflection is significantly reduced when the dry line appears on the surface of the sheet or pad. This substantial reduction of beam reflectance corresponds to the B break.

Any remaining free water is removed in the B–C segment of the tracing. Air flows through the mat pulling out still more water. After a certain point, air is pulled substantially freely through the mat. At this point, the web can no longer be dewatered by vacuum forces alone and typically enters the pressing section of the paper machine. This point is marked on the FIG. 4 tracing as the third point of inflection, point C. The amount of water removed in the A–C zone can be used to estimate pump capacities and storage in that zone. The longer the B–C zone in time, the greater the amount of vacuum required to completely drain the furnish.

Point C is correlatable with the ideal condition of the web at the couch of the paper machine, i.e., just before departure of the web from the forming section into pressing. By determining the percent solids of the system at point C, a theoretical maximum obtainable solids value is calculable which, when compared with actual machine values, constitutes a measure of wire or former efficiency.

The time recorded to reach a first point of inflection A is most sensitive to furnish species and wood pulp manufacturing processes, including chemical additives and fines content of the furnish. The first phase of drainage is also limited by characteristics or conditions of the water present, such as viscosity or height of water with respect to the forming wire. The appearance of point A is a unique characteristic of each pulp furnished. The time, in seconds, required to reach point A from the establishment of constant vacuum is called the "Drainage Number" of a pulp furnish.

In the embodiment of the invention described in the following examples, the drainage time means the elapsed time until the B break. This definition of drainage time is used because the B break can be detected by an optical sensor that determines when the reflectance from the sheet diminishes as the water disappears through the sheet.

The objects and function of the process of the present invention will be better understood by reference to the following examples.

The present system evaluates the effect of such variables as type of mixing, mixing time, and the amount and order of addition of chemicals on the physical behavior of a furnish. A family of physical behaviors are plotted as a function of time to provide information to the operator of a papermaking machine about optimal parameters of the papermaking process. The operator can use this information to maximize desired characteristics of a paper product made from the pulp.

EXAMPLE I

An initial set of studies (FIG. 5) was carried out using a 60/40 bleached hardwood Kraft/bleached softwood Kraft mix of stock (from the Weyerhaeuser Prince Albert Paper Mill) refined to three different freeness levels: 500 cc CSF, 425 cc CSF, and 350 cc CSF. With the three pulps, a study was carried out to show the effect of the chemical addition pattern on retention of the pulp. In this and subsequent studies, chemicals and addition patterns were followed that were recommended by the supplier of the additives (American Cyanamid). The distribution of the chemical additives through the furnish in this example was turbulently induced by the mixer 34. The speed of the mixer was set to about 100 RPM to achieve a type of mixing that corresponded to turbulent introduction of additives into a paper line. The addition pattern is shown in Table I below:

TABLE I

| Chemical Addition Pattern for Example I (FIG. 5) | |
|---|---|
| Samples #1 & 2 | Control (Fiber only) |
| Sample #3 | Taken 5 min. after the addition of 2 pounds/ton Cypro 515 |
| Sample #4 | Taken 5 min. after the addition of PCC (20% by weight of fibers) |
| Sample #5 | Taken 5 min. after the addition of Cationic Starch (8 pounds/ton) |
| Sample #6 | Taken 30 sec. after the addition of Retention Aid (Accurac 171) |
| Sample #7–#12 | Taken at 3 min. intervals following the addition of the Retention Aid |

As shown in Table I, two sequential aliquots of pulp from container 12 were sent to test container 16 (as samples 1 and 2) where they were formed into sheets on screen 86. The sheets were then removed from the screen and analyzed non-destructively to determine the grams PCC in the sheet. After PCC retention was determined as a control for Samples 1 and 2, the chemical addition pattern included the initial addition of a low molecular weight, high charge density polymer (Cypro 515) at a rate of two pounds per ton (based on the weight of fibers in the system). The polymer was allowed to mix for five minutes with the furnish and then sent to test container 16 as Sample 3. Next, precipitated calcium carbonate (PCC) was added at a level to give 20% pigment to the system. As with the Cypro, the PCC was allowed to mix for five minutes before an aliquot was sent to the metering head for analysis as Sample 4. The next additive provided to the mixture was cationic starch (Accosize 80, cationic potato starch from American Cyanamid) which was added to the level of eight pounds per ton. On a paper machine, the cationic starch is used to emulsify the sizing agent. Five minutes were allowed to elapse subsequent to the addition of the starch, and an aliquot was then sent to the metering head for analysis as sample number 5.

An anionic retention aid (Accurac 171 from American Cyanamid) was then added at a level of 0.5 pounds per ton. Generally, this type of polymer is added after the stock has passed the last shear point (the low density screens) in the average paper making system. The first aliquot for analysis (Sample 6) was taken thirty seconds after the polymer was added, because the time interval is short on a paper machine between the addition of this type of polymer and the coming of the furnish into the former section. Subsequent aliquots were withdrawn for analysis as three minute intervals (samples 7-12).

Figure 5:
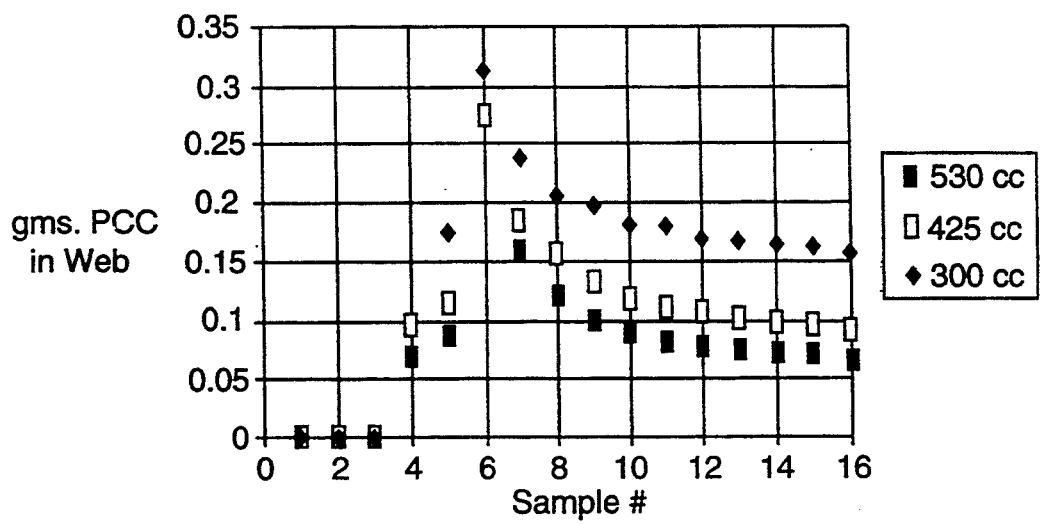
FIG. 5 is a plot of the pattern of PCC retention as a function of stock freeness and mixing time with turbulent distribution of chemical additives to a pulp slurry sample in Example I.

The change in PCC retention as a function of time after mixing the chemicals with the furnish is shown in FIG. 5. In the system that approximates turbulent addition to a paper line (where mixing was made efficient by high speed rotation of mixer blade 40), the retention of pigment peaked within thirty seconds after the anionic retention aid was added to the system (sample in FIG. 5). Peak retention of PCC was relatively close with all three furnishes (300, 425 and 530 cc freeness). This indicates that the size of the PCC flock was at a maximum in size at the thirty second mixing time. As mixing continued beyond the peak, the freeness of the stock increasingly became a stronger factor in determining retention. As the size of the flock decreased, the geometry of the pad became more of a factor in determining retention. Toward the end of the test, PCC retention approaches that level noted before the addition of the anionic retention aid (compare sample 16 with sample 5). The data also show that cationic starch has a positive but small effect on PCC retention (sample 5).

Figure 6:
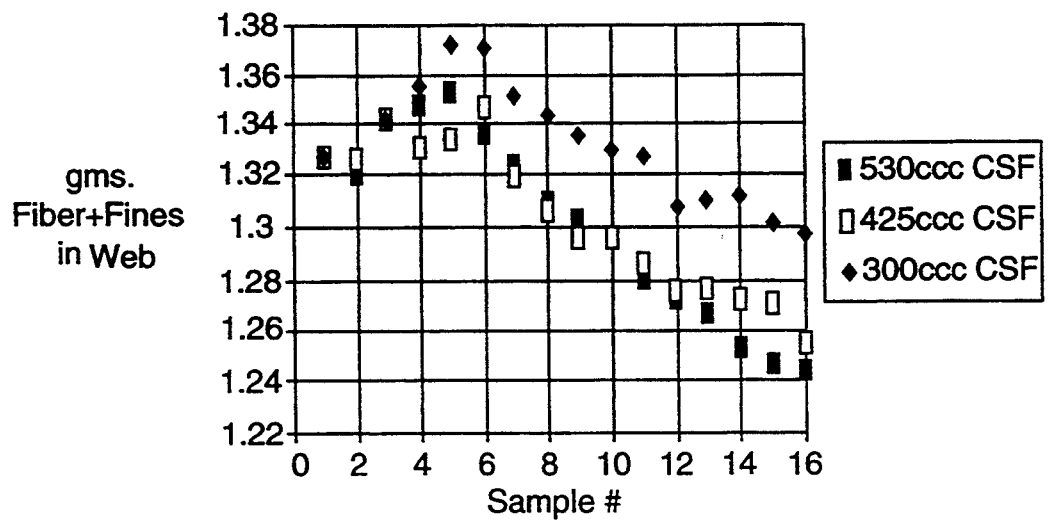
FIG. 6 is a plot of the pattern of fines and fiber retention as functions of stock freeness and mixing time with turbulent mixing of chemical additives in the pulp slurry sample of Example I.

Fiber and fines retention in this set of experiments is calculated from the grams of PCC in the webs, and is shown in FIG. 6. Fiber/fines retention was calculated by subtracting the grams of PCC in the web from the weight of the web. Each sample number in FIG. 6 corresponds to the sample addition pattern shown in TABLE I. This graph shows that the fiber retention pattern in a turbulence controlled system tends to follow that of PCC. The fiber/fines retention decreases with time, however, below that noted with the control (Samples 1 and 2). This pattern suggests that the free energy of the initial reaction products is low, hence the final reaction product is probably governed by free energy considerations instead of collision theory (turbulent mixing) alone. Such a result would alert a paper line operation that fines and fiber retention can decline on a paper line if, after additives are turbulently introduced into the line, too much time is allowed to elapse until the pulp is dewatered on the wire. This pattern is especially important when compared to FIG. 5, where PCC retention does not decline below a control. These results show that as time passes on a paper line, fines and fiber retention will diminish more than pigment retention. These patterns tell a papermaker where to add chemicals to optimize fines and pigment retention.

EXAMPLE II

The effects of reducing RPMs of blade 40 were studied in this Example, and the results are reported in FIGS. 7-12. Reducing the speed of blade 40 more closely imitates the reaction kinetics of introduction of additives by passive diffusion on a paper line. It is preferable to reduce the speed of the mixing blade without stopping it altogether because minimal blade rotation helps achieve a uniform suspension of slurry throughout the depth of the sample in container 12. In this example, the speed of the blade 40 was approximately 10 RPM.

Figure 7:
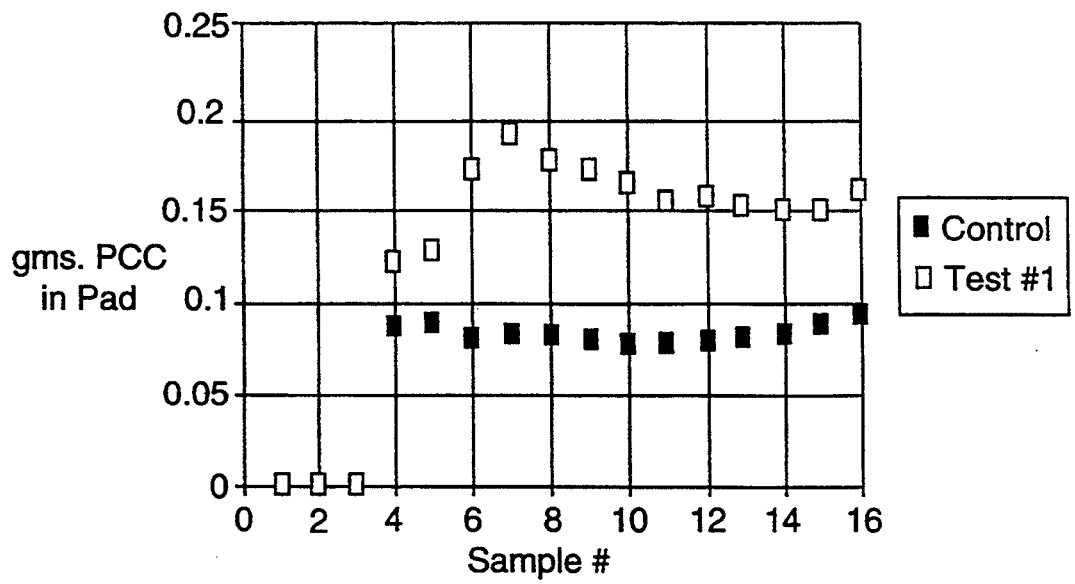
FIG. 7 is a plot of the pattern of pigment retention (PCC) in a neutral alkaline chemical furnish after addition of chemical additives with primarily diffusion controlled reaction kinetics achieved by minimal mixing of the furnish and additives in Example II.
Figure 8:
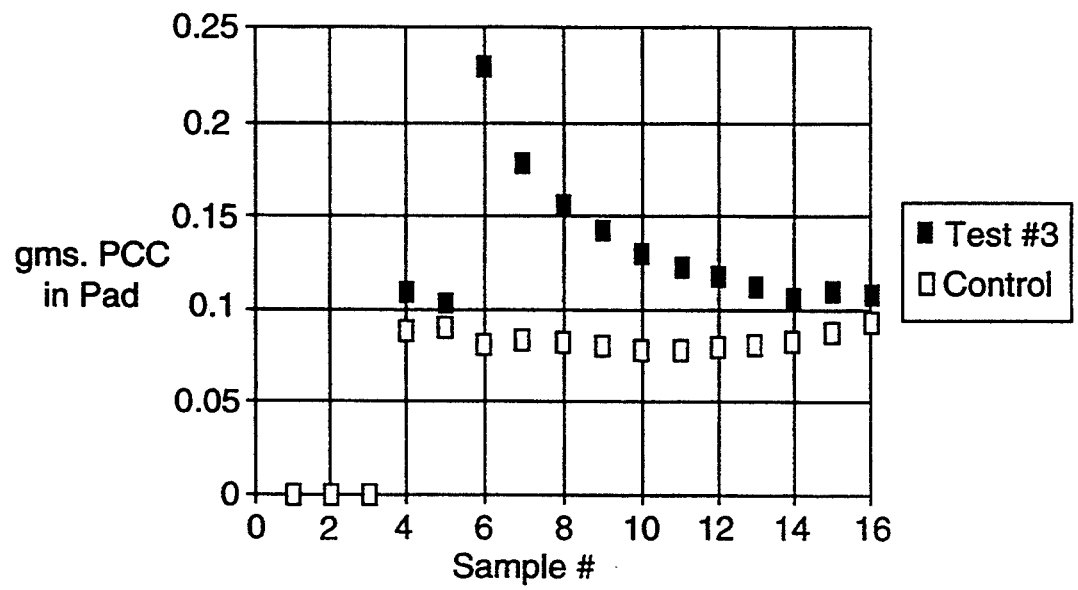
FIG. 8 is a plot similar to FIG. 7, but with reaction kinetics obtained by turbulently mixing the additives with the furnish at a higher mixing blade speed in Example II.
Figure 9:
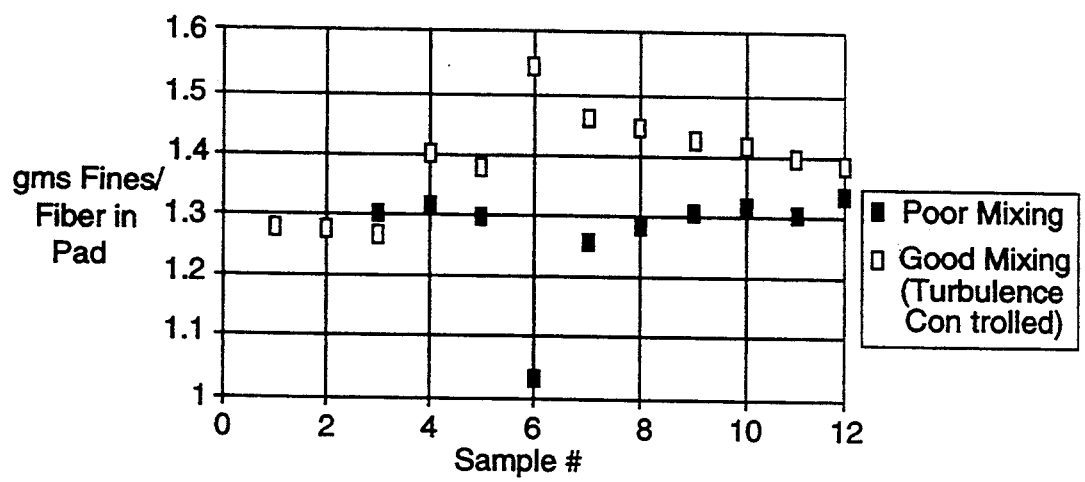
FIG. 9 is a plot comparing fines/fiber retention in a neutral alkaline system after addition of chemical additives at low mixing blade speed (poor mixing) and at higher blade speed (good mixing) in Example II.
Figure 10:
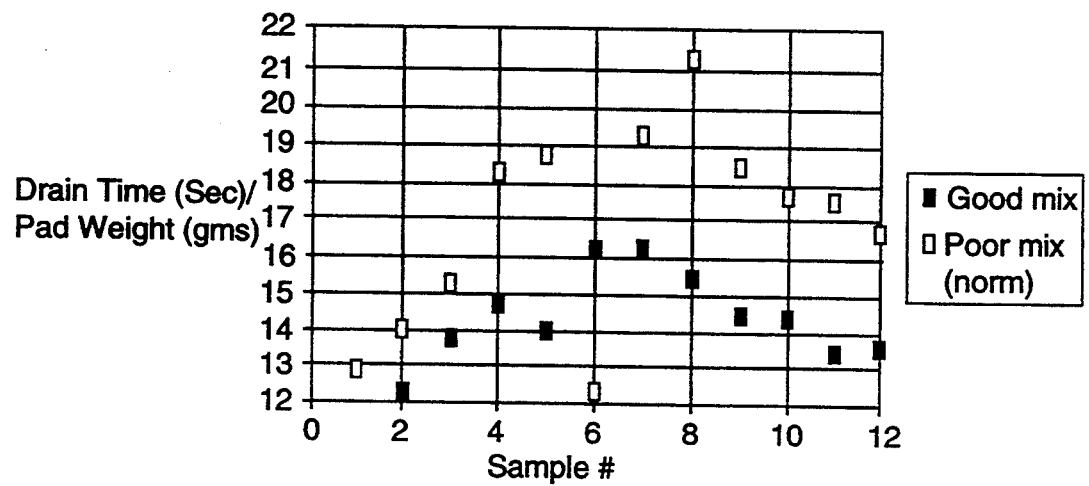
FIG. 10 is a plot of drainage time of individual samples in a neutral alkaline system at discrete time intervals after the addition of chemical additives, comparing the patterns obtained with both good and poor mixing in Example II.
Figure 11:
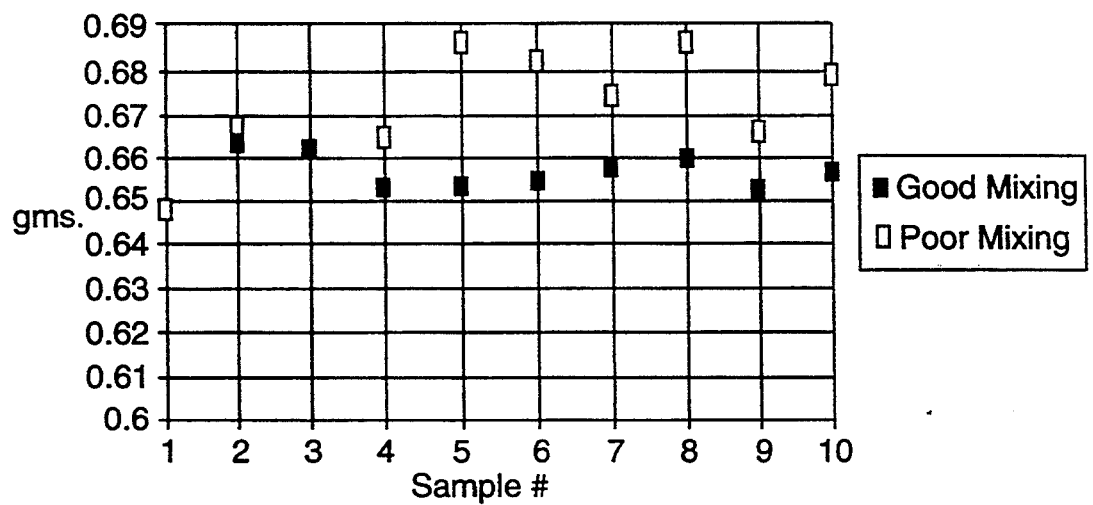
FIG. 11 is a plot of total pad weight versus sample number that shows the effect of good and poor mixing on fines retention in a mechanical pulp after addition of 0.5 pound of a high molecular weight, low cationic charge density polymer in Example III.
Figure 12:
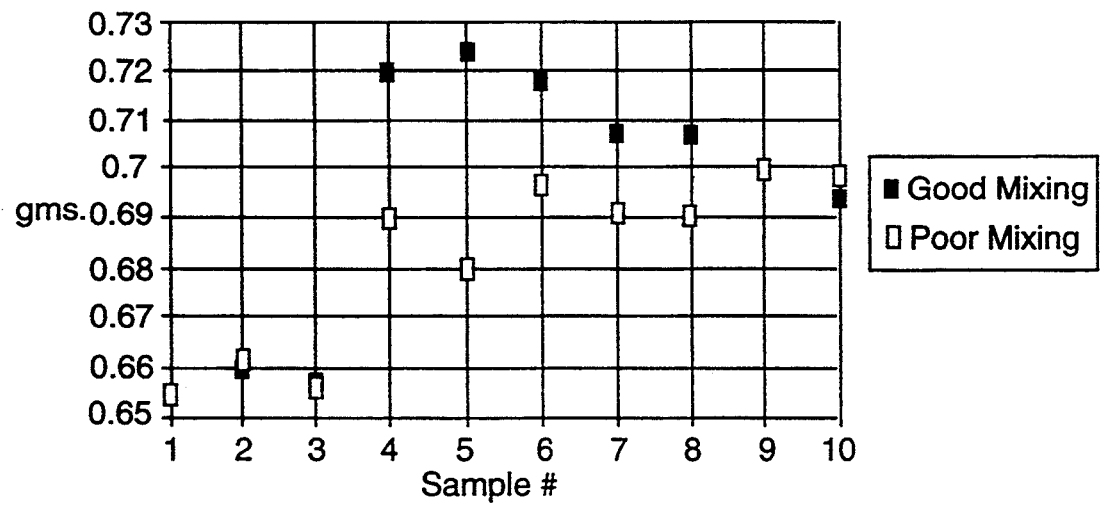
FIG. 12 is a plot similar to FIG. 11 showing the effect of mixing on retention after a 1 pound per ton polymer addition in Example III.

The study was carried out using two furnishes; the first was a chemical furnish and the second was a mechanical furnish. The chemical furnish was a neutral alkaline chemical pulp/PCC furnish, similar to that used in Example I above, and for which the results are shown in FIGS. 7-10. The mechanical furnish is described in Example III below, and the results are shown in FIGS. 11-12. The pattern of grams PCC in the pad shown in FIG. 7 was obtained with poor mixing of additives in the chemical furnish, while the pattern of PCC pigment retention in FIG. 8 was produced by increasing the speed of mixing blade 40 to about 100 RPM and achieving good mixing. The control run in both FIGS. 7 and 8 was a furnish to which no additives were supplied, but that was subjected to the same type and duration of mixing as the studied furnish. FIG. 9 shows grams of fines/fiber in the pad as a function of sequential sample number with both high speed (good) mixing, and low speed (poor) mixing, following the addition pattern of Table I. FIG. 10 shows the drain time/pad weight in seconds as a function of sample number for the furnish of Example I with both good and poor mixing in container 12, following the addition pattern of Table I.

The results of the study with chemical pulp show that the PCC retention pattern was essentially the same with good mixing (FIG. 8) and poor mixing (FIG. 7) in that both patterns peaked within thirty seconds after the addition of the anionic polymer (sample 6). However, the set with good mixing (FIG. 8) peaked at higher retention value than did the set with poor mixing (FIG. 7). The set with poor mixing (FIG. 7) showed a slower decrease in retention as mixing continued than did the set with good mixing (FIG. 8). The fines retention pattern (FIG. 9), however, was more dependent on the mode of mixing. With good mixing, fines retention peaked close to that of the PCC retention. With diffusion type mixing (poor mixing in FIG. 9), fines retention tended to peak at a significantly longer mixing time than that of the PCC. With good mixing, fines retention also improved by about 20-25%. With poor mixing, the improvement was in the range of 5%. Quite significantly, the peak of retention in FIG. 9 with good mixing actually corresponded to a trough in retention for poor (diffusion-like) mixing. The drain time patterns (FIG. 10) show that good mixing (which corresponded to turbulent addition on a paper line) gave retention with relatively fast drainage, whereas diffusion-type (poor) mixing gave retention with a slowing or prolongation of drainage time.

These results illustrate the benefit of studying a family of physical behavior relationships. If PCC retention alone is studied (FIGS. 7 and 8), an operator may conclude that the type of mixing on a paper line is not a factor that significantly influences the behavior of the pulp and the characteristics of the sheet. The similar reaction patterns of FIGS. 7 and 8 do not suggest that the pattern is influenced by the kind of mixing. The fines and fiber retention patterns of FIG. 9, however, show that the type of mixing has a significant effect on the kind of retention. If poor mixing is used, fines/fiber retention will be at a trough as pigment retention peaks. Hence, good turbulent mixing on the paper line will be desired if a product is desired having maximum pigment and fines/fiber retention.

EXAMPLE III

FIGS. 11–12 show the effect of "good mixing" (high RPM or turbulent addition) or "poor mixing" (low RPM or passive addition) on pad weight in grams for a mechanical pulp furnish (TMP from NORPAC). The addition and measurement pattern for the mechanical pulp furnish was different than that described in Table I above. For the mechanical pulp furnish, the only chemical added was a high molecular weight, low cationic charge density polymer (Diabond TM) manufactured by Diachem. The addition pattern is shown in Table II below:

TABLE II

Sample Pattern for Addition of Polymer to Mechanical Stock (FIGS. 11–12)

| Samples | Pattern |
| --- | --- |
| Samples #1, 2, and 3 | Controls |
| Sample #4 | Taken 30 seconds after Diabond addition |
| Samples #5–10 | Taken at 3 minute intervals |

Figure 13:
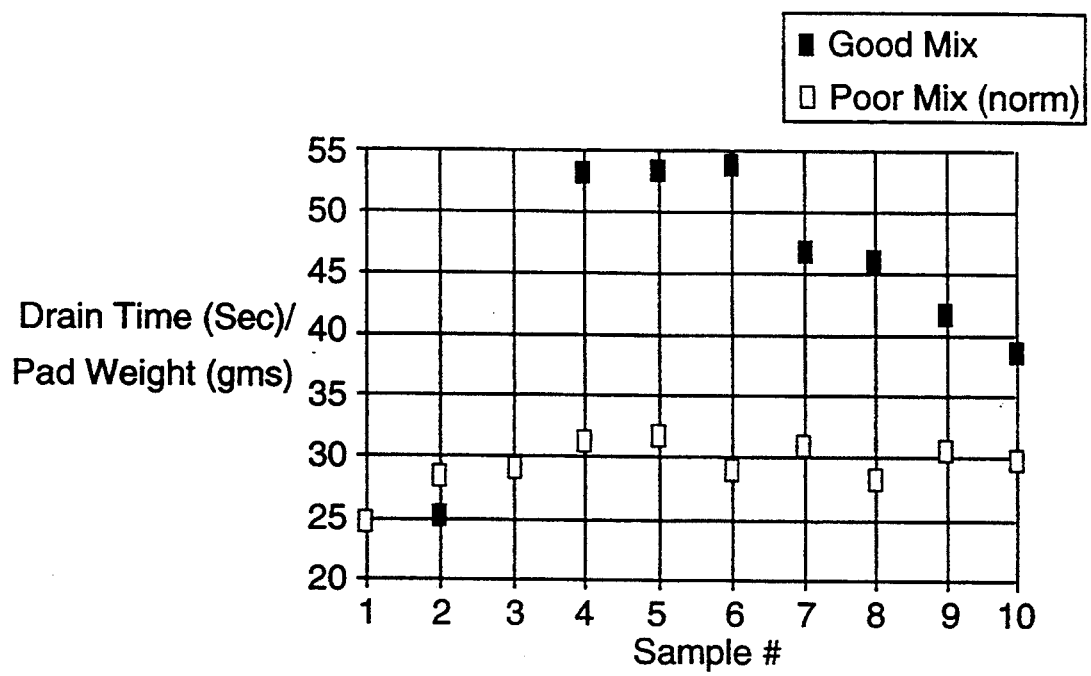
FIG. 13 is a plot showing the effect of good and poor mixing on drainage time after addition of 0.5 pounds per ton of the polymer to a mechanical pulp in Example III.
Figure 14:
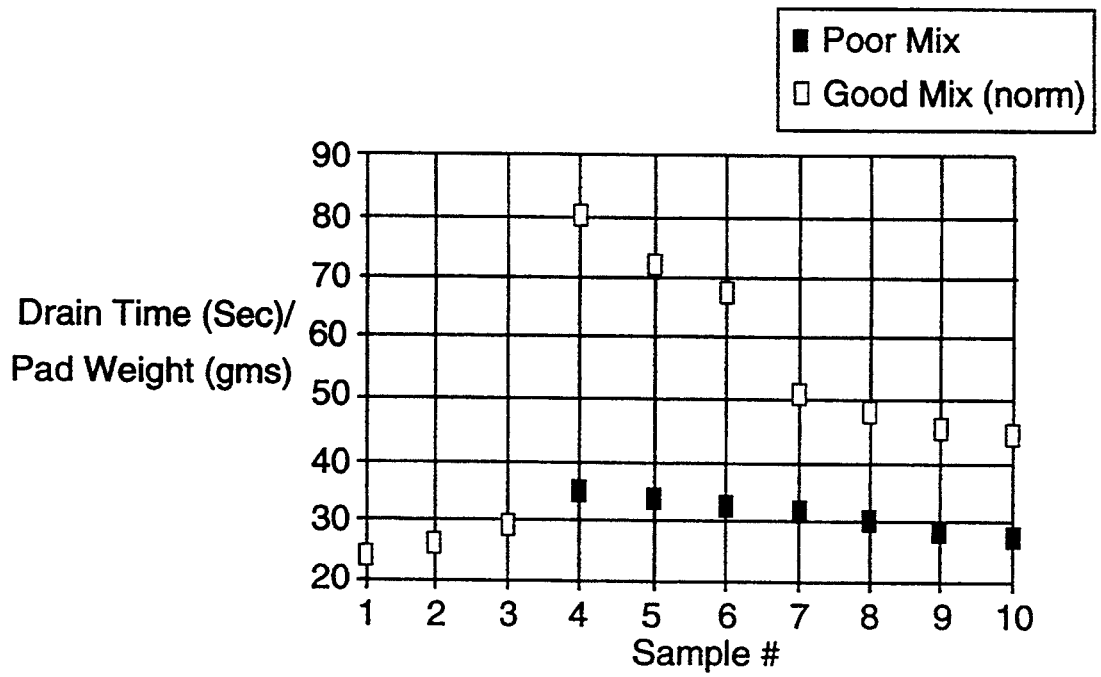
FIG. 14 is a plot similar to FIG. 13 after addition of 1 pound per ton of the polymer in Example III.

In this Example, the effect of a Diachem addition on fines retention is shown. The drainage of a mechanical pulp with a minimum of pigment (less than 2%) and a maximum of fines was followed as a function of mixing time. A mechanical pulp furnish differs from a bleached chemical pulp furnish in that there is a difference in the fiber morphology, and the mechanical pulp furnishes have a significant quantity of anionic carryover (from the defibering process) in the system. The results of the study with the mechanical pulp are presented in FIGS. 11–14. In the runs of FIGS. 11 and 13, Diachem was added in an amount of 0.5 pound per ton of slurry. In the runs of FIGS. 12 and 14, Diachem was added in an amount of 1.0 pound per ton.

In the studies with the TM pulp, samples 1, 2 and 3 (FIGS. 11–14) are control samples in which no polymer has been added. Sample 4 was taken thirty seconds after addition of the polymer, and the remaining samples were taken at three minute intervals. As seen from FIG. 11, retention at a chemical dose rate of 0.5 pounds per ton was optimized in that system where the distribution of the polymer was diffusion controlled. In other words, mixing blade 40 ran at about 10 RPM. Retention was diminished when good mixing (about 100 RPM) was used. This result shown in FIG. 11 is interesting in view of the study with the chemical pulp/PCC furnish (FIGS. 7–10), in which the opposite result was found. Good mixing in those examples maximized retention. It is unexpected that turbulence type mixing decreases retention at this level of polymer addition.

The difference in these results could be explained by anionic carryover in the TM pulp. In a turbulence controlled distribution system, the first reaction of the cationic polymer is with the most mobile and anionic element, the anionic carryover. When this occurs, the cationic polymer is neutralized and unavailable to react with the anionic fibers. Conversely, in a diffusion controlled distribution system, there are zones of relatively high cationic polymer concentration. In these zones, there is sufficient polymer to both react with the anionic carryover and with the anionic fibers. From the results of this study, it appears that in systems containing anionic carryover, where the dose of the polymer to be used is insufficient to both react with the anionic carryover and fibers, the diffusion method of distribution produces a positive effect.

This conclusion is supported by the data shown in FIG. 12 where the dose of cationic polymer was increased to one pound per ton of the Diachem product. Here, the retention pattern is similar to that seen in the neutral/alkaline papermaking system (FIG. 8). Good mixing, which approximates turbulent addition of polymer on a paper line, produces better retention in the product. Based on these results, it appears that the one pound per ton dose of polymer was sufficient to both react with the anionic carryover and the fibers in the system. Conversely, the 0.5 pound per ton dose of polymer was not sufficient to react with both the anionic carryover and the fibers.

Drainage, in contrast, was slowed to the greatest extent in that furnish where the polymer addition was turbulently distributed (with "good mixing" in FIGS. 13 and 14).

Figure 15:
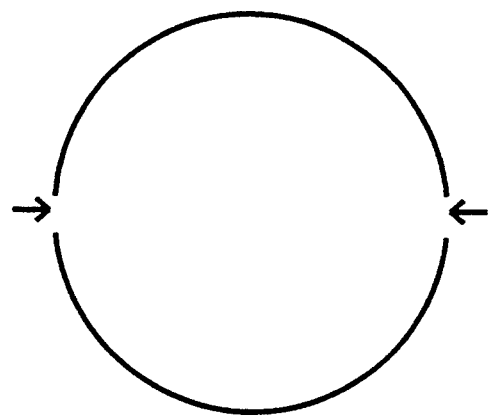
FIG. 15 is a schematic view of a method of adding retention aids to a slurry conduit on a paper line with poor mixing such that reaction kinetics tend to be diffusion controlled.

The patterns of FIGS. 11–14 point out the importance of knowing the mixing pattern of chemicals in papermaking furnishes. In many paper mills, there is little or no mixing of the system after the addition of the high molecular weight, low charge density polymer and thus the spread of the polymer through the system tends to be diffusion controlled. In a mill having diffusion controlled mixing, it will be important to select a level of polymer addition that will be sufficient to react with both the anionic carryover and the fibers in the system. The amount of polymer addition will not be as important a factor in turbulence controlled mixing lines. An example of a paper line system that is diffusion controlled is shown in FIG. 15 where polymer is added to the system through taps in the side of the pipe. Under these conditions, the distribution of the polymer tends to be diffusion controlled because there is little mixing in this part of the papermaking system.

Figure 16:
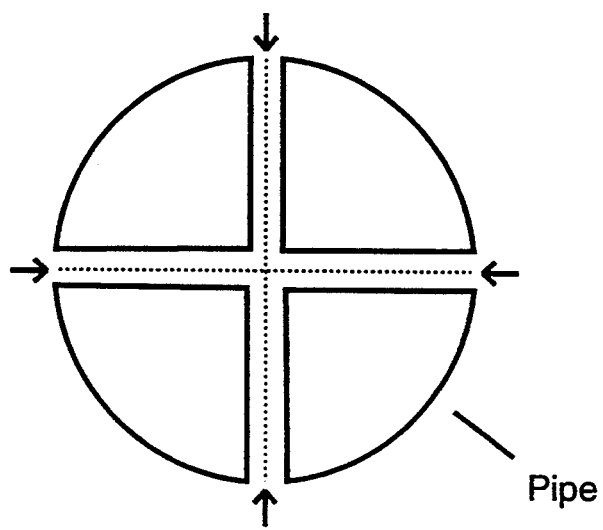
FIG. 16 is a schematic view, similar to FIG. 15 showing means of adding retention aids with good mixing to a paper line.

In other paper mills, the polymer is added to the furnish through a tubular cross in the line (FIG. 16) that has a series of orifices through which the additive is introduced into the line. Although the mixing of the polymer with the furnish is diffusion controlled, the addition pattern is such that the polymer is well mixed with the furnish. In this situation, the end result is the same as if the distribution were turbulence controlled. The results of the good mixing runs will then apply. In those systems containing a step diffuser in the head box, the distribution of the polymer is turbulence controlled because a step diffuser is a shear point.

EXAMPLE IV

In this one study, the retention of calcium carbonate in a system containing fiber and calcium carbonate (20% by the weight of fibers in the system) was followed as a function of the time of the mixing of a furnish with an anionic polyacrylamide retention aid added at a level of 1 pound/ton.

The open marks are those samples to which the anionic retention aid was added. The closed samples are those of the control furnish (fiber+calcium carbonate and no retention aid).

Figure 17:
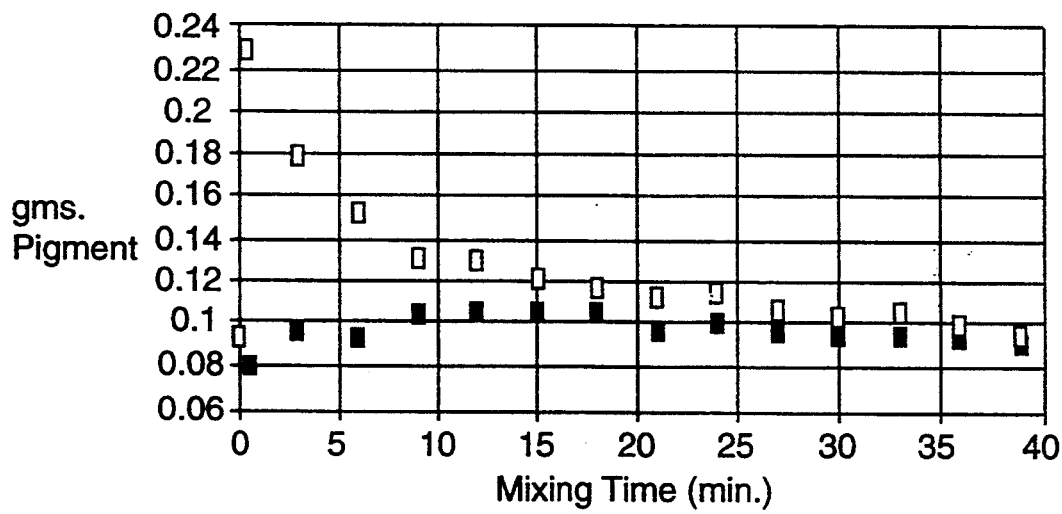
FIG. 17 is a graph showing calcium carbonate retention as a function of mixing time after the addition of an anionic polymer retention aid in Example IV.

The graph of FIG. 17 shows that pigment retention decreases rapidly with mixing. This result suggests that rapid dewatering of the pulp is desireable on the line to stop the reaction if good pigment retention is desired.

EXAMPLE V

Figure 18:
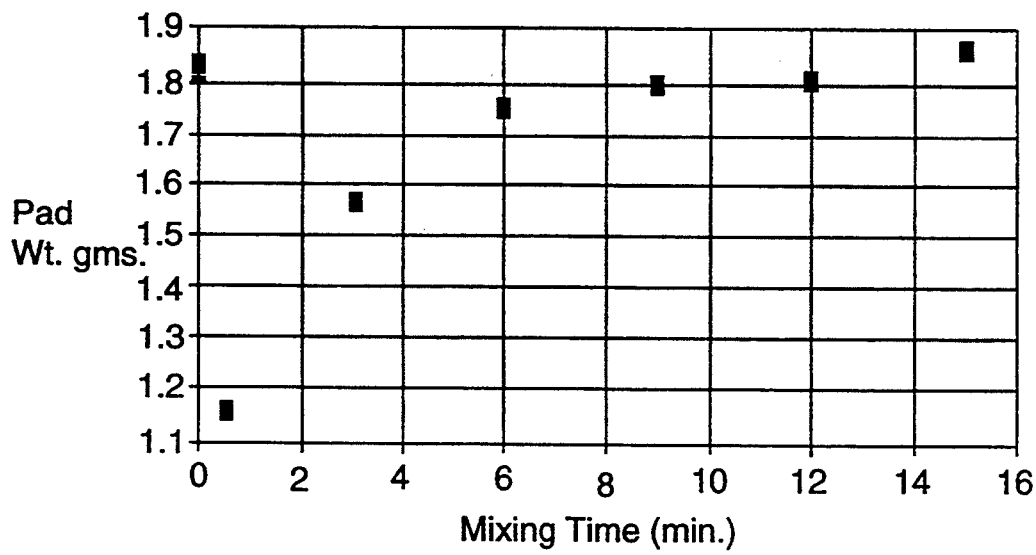
FIG. 18 is a graph showing the effect of a cationic polymer on total retention as a function of mixing time after addition of the polymer in Example V.
Figure 19:
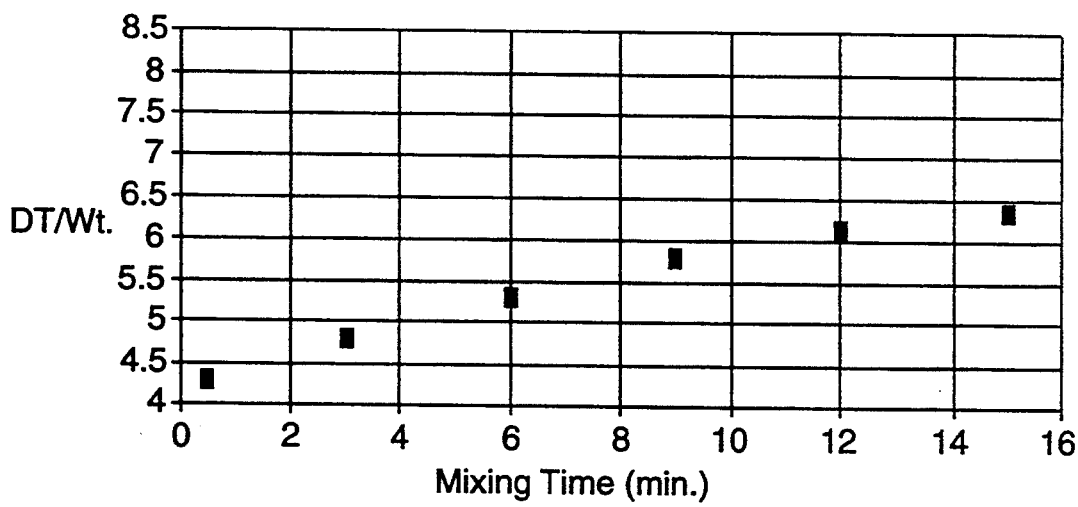
FIG. 19 is a graph similar to FIG. 18 showing the effect of mixing time on drainage time/weight in Example V.
Figure 20:
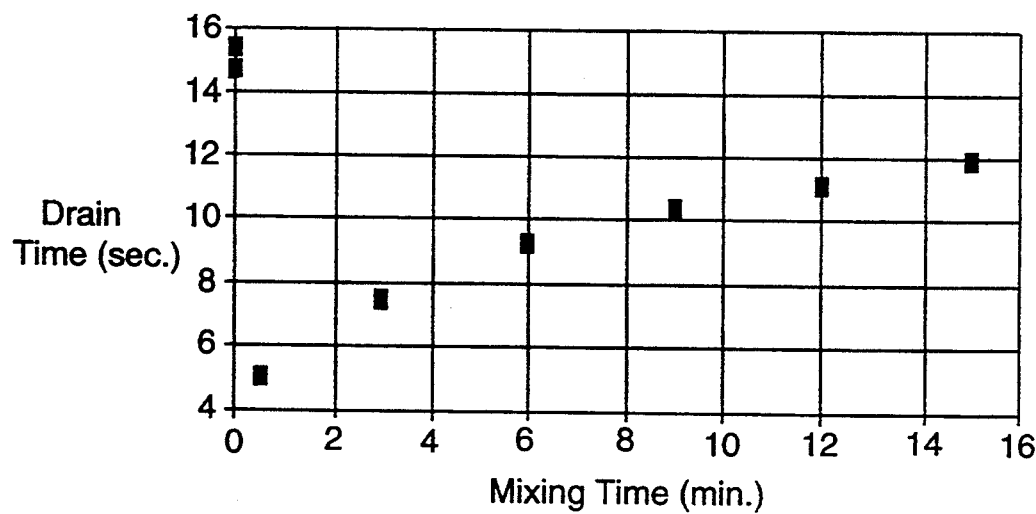
FIG. 20 is a graph similar to FIG. 19 showing the effect of mixing time on drainage time in Example V.
Figure 21A:
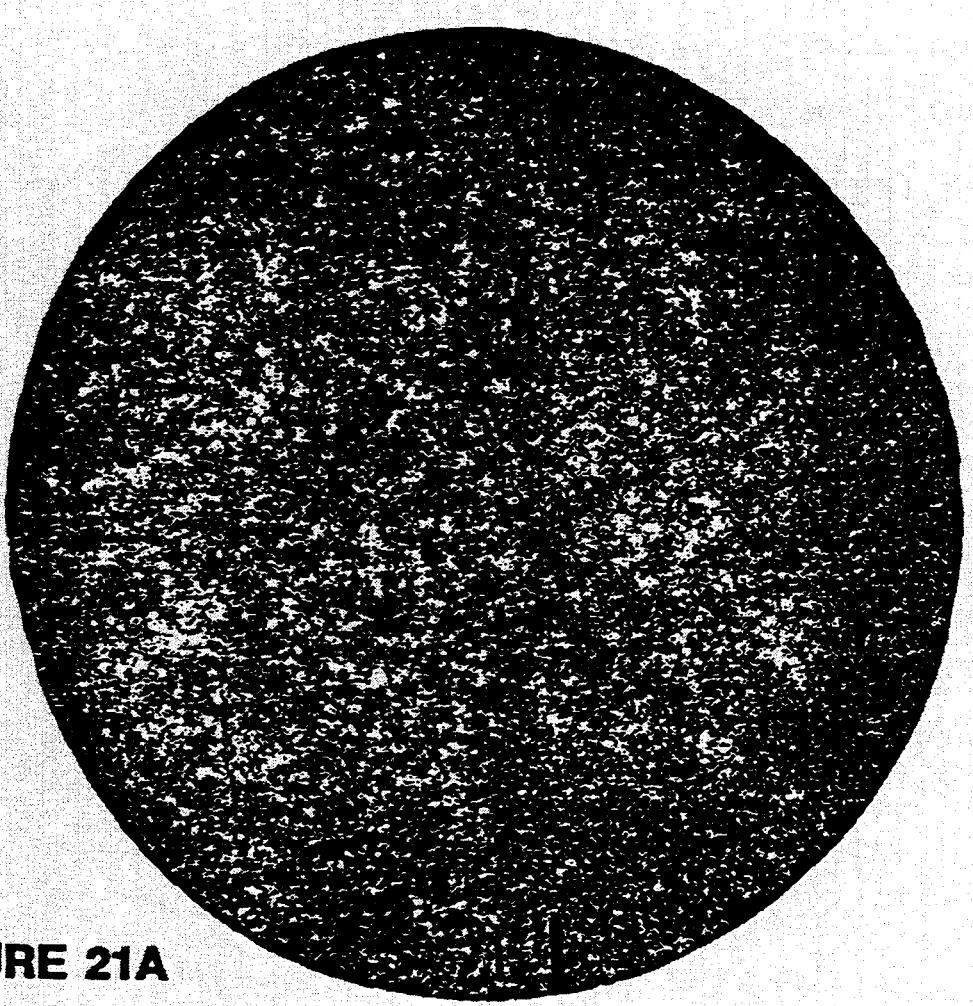
FIGS. 21A, 21B, 21C, 21D, 21E, 21F and 21G are copies of sheets showing the visual characteristics of sheets obtained in Example V after mixing times of zero and 30 seconds, and at subsequent three minute intervals thereafter.
Figure 21B:
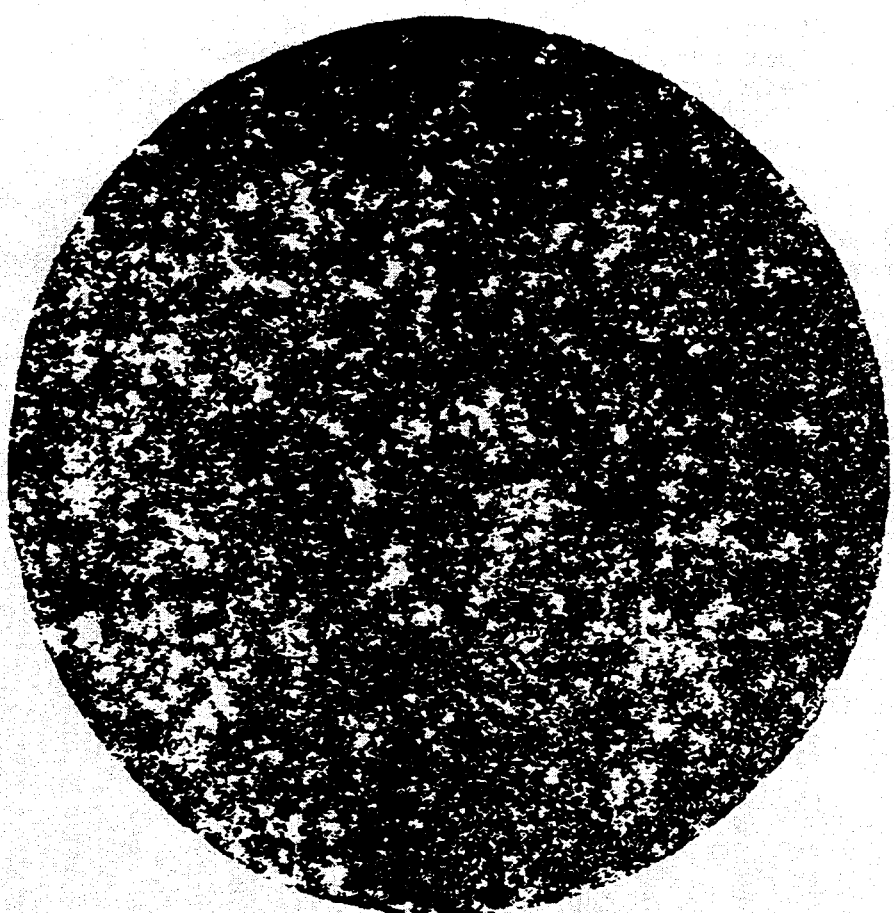
Figure 21C:
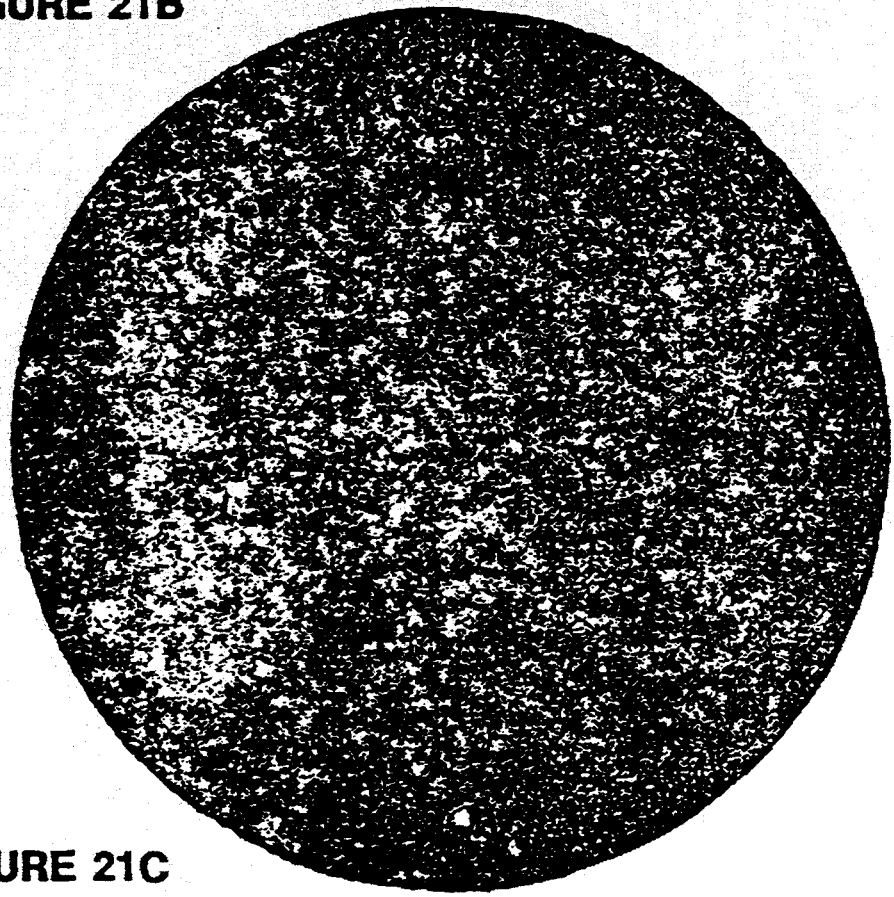
Figure 21D:
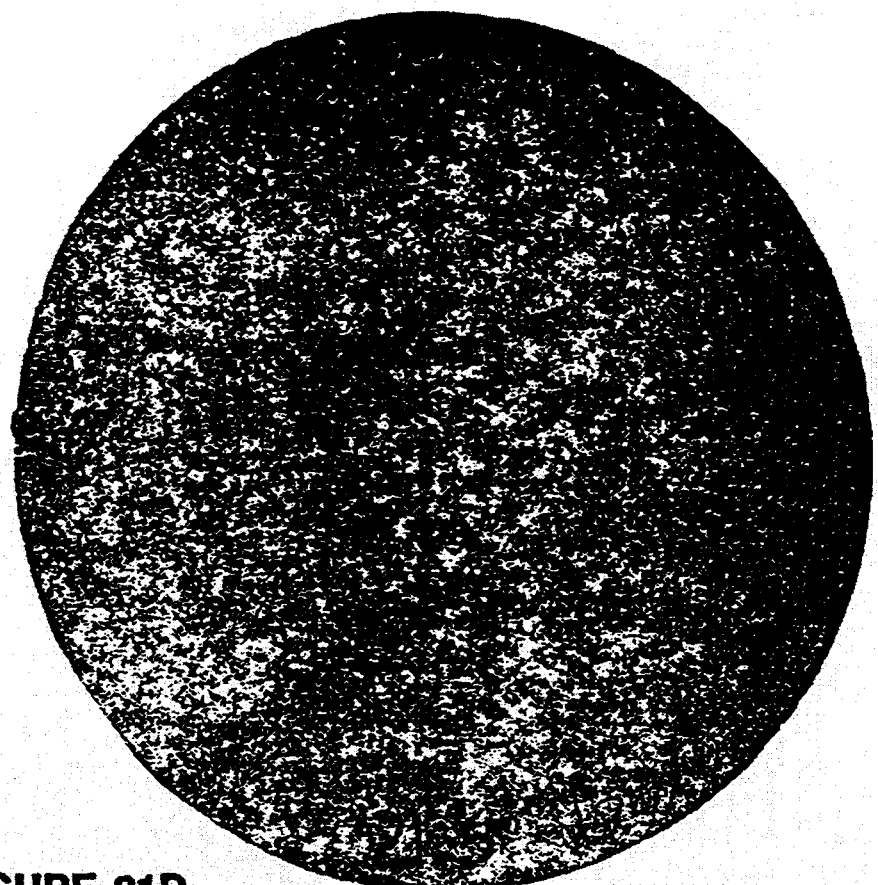
Figure 21E:
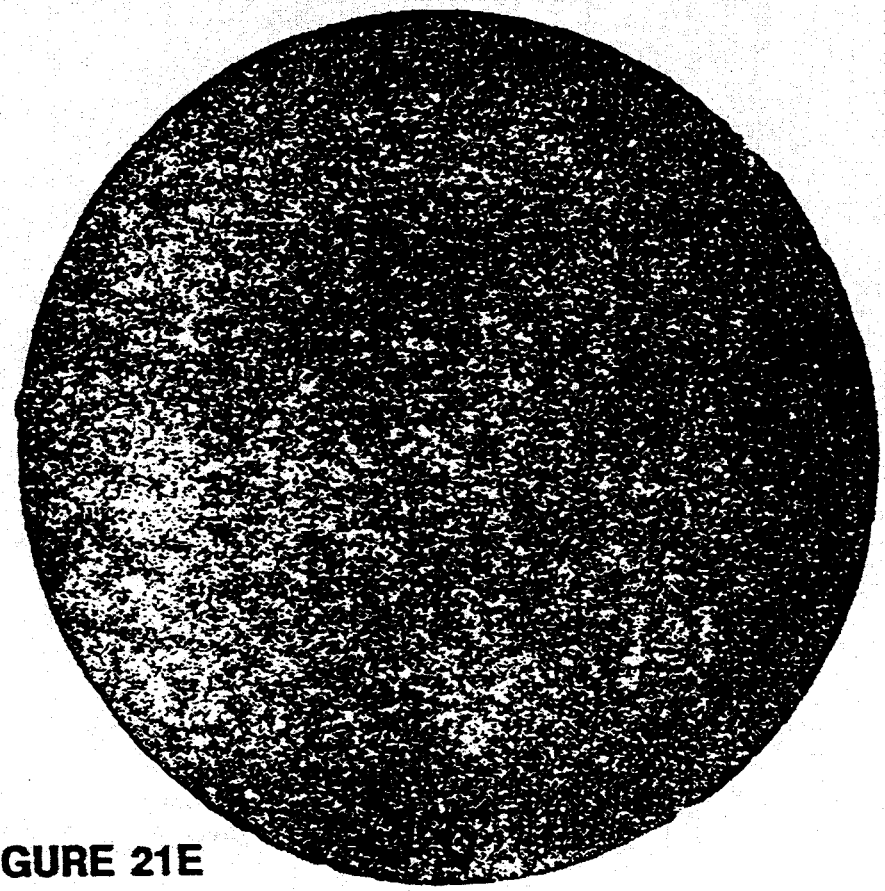
Figure 21F:
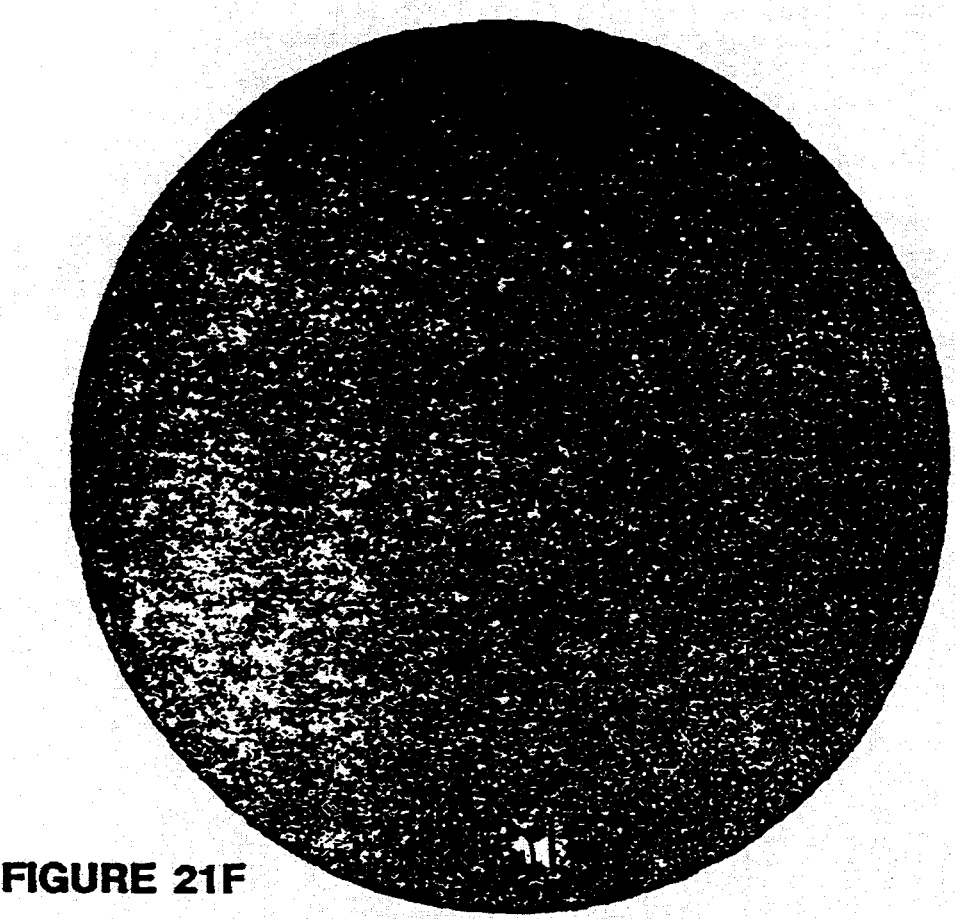
Figure 21G:
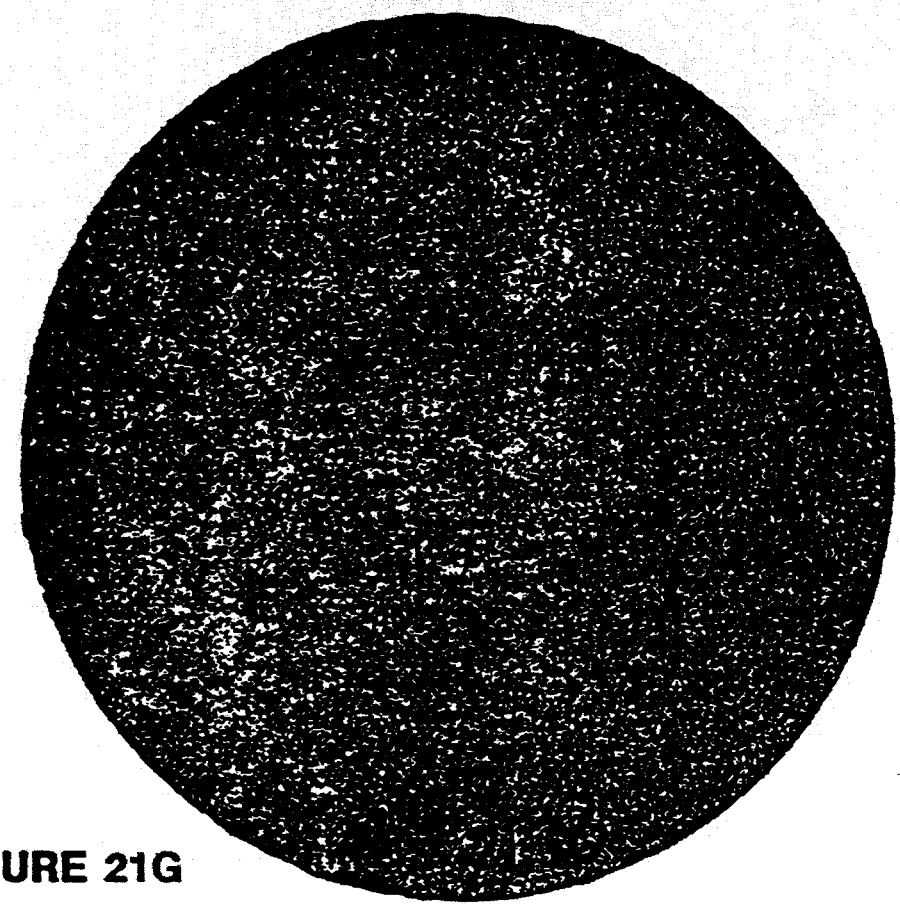
Figure 22:
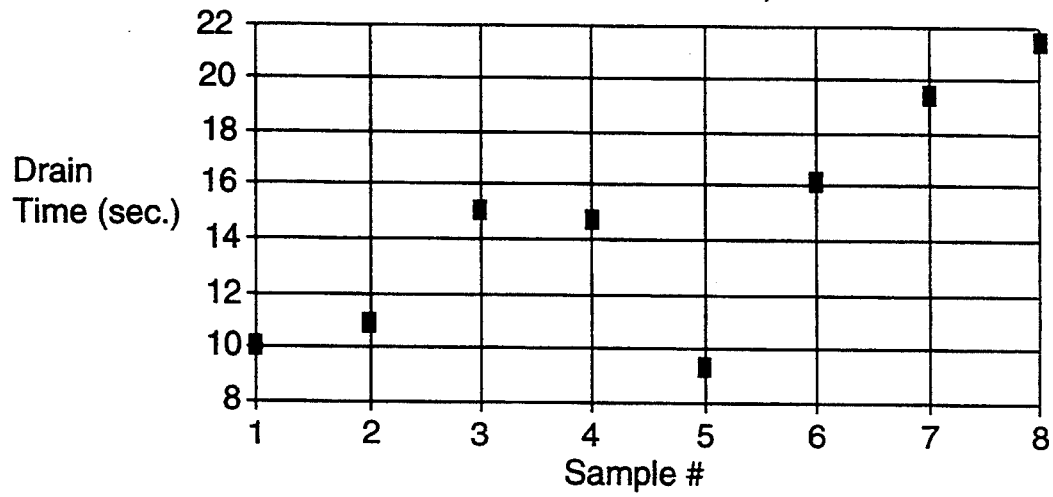
FIG. 22 is a graph of the results of Example VI showing the effect of a cation/anion retention aid system on furnish drain time.
Figure 23:
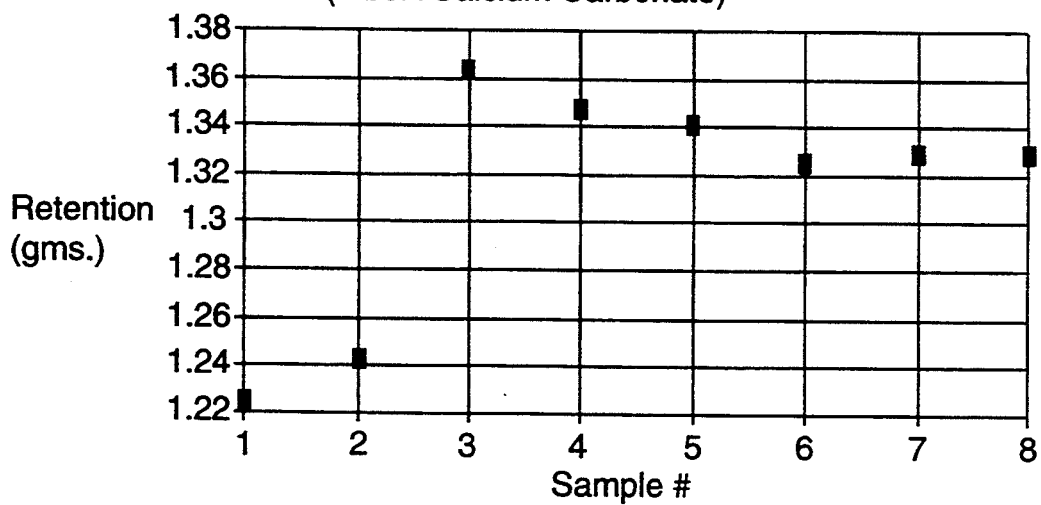
FIG. 23 is a graph similar to FIG. 22 showing the effect on fines retention.

In this example, the effect of a high molecular weight cationic polyacrylamide on a furnish containing only fibers was determined. No pigment was added to this furnish and the experiment was carried out at a pH of close to 7.0 and 2 pounds/ton of the cationic polyacrylamide was used. The data at zero time is the control (no retention aid; fiber only) and the formation pattern of the sheet formed at that time is shown in FIG. 21A. The effects of polyacrylamide addition are shown on Fiber/Fine retention (FIG. 18), Drain Time/Weight (FIG. 19) and Drain Time (FIG. 20). The formation sample shown in FIG. 21B was from that test taken 30 seconds after the addition of the cationic retention aid. The samples shown in FIGS. 21C to 21G were taken at subsequent 3 minute intervals.

The visual appearance of FIGS. 21C-21G shows the immediate decrease in formation after the addition of the retention aid and the improvement in formation as mixing continued. This data shows that the reaction of chemicals with the elements of papermaking furnishes is not a simple one-step reaction. Pad weight and drain time decreased precipitously after initial additive introduction, and gradually improved with mixing throughout the remaining range of the data. The visual appearance of resulting sheets also followed this pattern. Hence the visual appearance of a formed sheet can be used as one of the family of relationships that changes with mixing as a function of time.

EXAMPLE VI

In the system described in FIGS. 22-26, the cation used was Polyethyleneimine at a dose of 20 pounds/ton, the anion used was an anionic polyacrylamide (Cyanamid Accurac 171) at a dose of 1 pound/ton, and the furnish used was Northern kraft refined to 250 cc CSF freeness to which had been added 20% by the weight of the fibers, of precipitated calcium carbonate.

Figure 26:
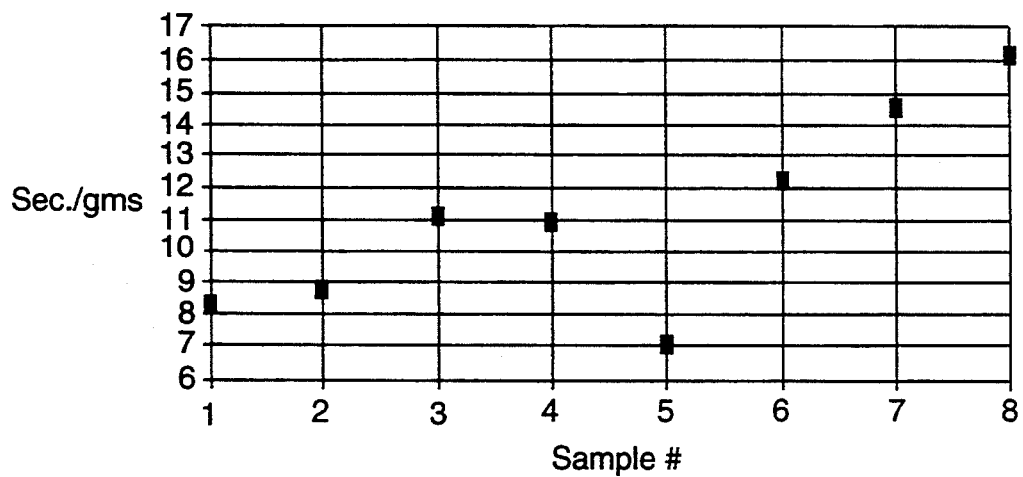
FIG. 26 is a graph similar to FIG. 25 showing the effect on drainage time/pad weight.

Samples 1 and 2 were taken after 5 and 8 minutes mixing respectively and are controls (no chemicals other than fiber and calcium carbonate). Samples 3 and 4 were taken after the addition of the cationic polymer (polyethyleneimine at a dose of 20 pounds/ton). The furnish was mixed for 5 and 8 minutes respectively prior to the taking of the samples for analysis. Sample 5 was taken 30 seconds after the addition of the anionic polymer (Accurac 171 at a dose of 1 pound/ton). Samples 6-8 were taken at three minute intervals subsequent to the taking of sample #5. FIG. 26 (Drain Time/Pad Weight) is a measure of a combination of fines retention and flocculation and must be examined knowing the degree of flocculation of the material forming the sheet.

Generally flocculation both decreases the fiber surface area/weight directly, due to the formation of the flocs, and indirectly by opening up the sheet and allowing the fines to pass through the mat that is being formed. As a result, one cannot determine (without further analysis) which factor predominates.

As used in this specification, the "behavior" of a pulp on a paper line refers to such properties as drainage time, pigment retention, fines retention and the visual appearance of a sheet. The phrase "prolonging reactions" refers to reacting the furnish with additives under conditions that cause the reactions to take longer than they would on a paper machine.

Having illustrated and described the principles of the invention in many preferred embodiments, it should be apparent to those skilled in the art that the invention can be modified in arrangement and detail without departing from such principles.

We claim all modifications coming within the spirit and scope of the following claims:

1. A method for evaluating a reaction pattern of a paper pulp furnish, the method comprising the steps of:
   placing the furnish in a holding container;
   combining an additive with the furnish in the holding container and mixing the additive and furnish to form a mixture thereof;
   transferring the mixture through a transfer line from the holding container to an intermediate container that maintains a substantially constant hydrostatic head on the mixture in the intermediate container by maintaining a substantially constant depth of the mixture in the intermediate container;
   transferring at preselected intervals of time an equal volume sample of the mixture from the intermediate container to a test container having a screen bottom for separating furnish solids from slurry water;
   dewatering each said equal volume sample in the test container to form a sheet therefrom by subjecting each said equal volume sample to a pressure differential created by providing a reduced pressure beneath the test container screen; and
   determining one or more properties of each said sheet that is related to the function of the additive that was added to the furnish to thereby determine the effect of the additive on the equal volume sample of furnish at each preselected interval of time wherein the one or more properties of said sheet is chosen from the group consisting of pigment retention, fines retention, drainage time and visual appearance.

2. The method of claim 1 wherein the combining step comprises prolonging a reaction of the additive with the furnish Such that the reaction requires longer to complete than on a paper line, by mixing the additive with the furnish while maintaining a substantially uniform mix in the holding container at a sufficiently low level of turbulence in the holding container to prolong said reaction.

3. The method of claim 2 wherein the mixing step comprises mixing the additive with the furnish using a horizontally rotating mixing blade having a shape that directs a portion of the furnish upward while the blade rotates to maintain a uniformly mixed mixture.

4. The method of claim 3 wherein the mixing step comprises mixing the additive and furnish with a mixing blade having a portion that rotates in a horizontal plane, the blade further including a first surface that is inclined to and extends above the horizontal plane and a second surface that is inclined to and extends below the horizontal plane.

5. The method of claim 1 wherein the additive has an effect on fines and pigment retention in the sheet formed from the furnish.

6. The method of claim 5 wherein the determining step further comprises determining the drainage time of each said sheet.

7. The method of claim 6 wherein the step of determining the drainage time of each said sample comprises providing liquid level monitors in the test container.

8. The method of claim 6 wherein the step of determining the drainage time of each said sheet comprises providing an optical sensor that senses changes in reflectance of the sheet.

9. The method of claim 8 further comprising recording the pressure differential across the sample as a function of time throughout the entire period when water is being removed from the sheet as it forms.

10. The method of claim 6 further comprising the step of recording a visual rating of the appearance of each said sheet after the sheet is formed.

11. The method of claim 10 wherein the drainage time of each said sample is determined by providing an optical sensor that senses changes in the reflectance of the sheet to sense a change in reflectance that indicates a wet line or a dry line.

12. The method of claim 1 wherein the steps of transferring the furnish to the intermediate container and test container comprise transferring the furnish with pumps that do not further mix the furnish.

13. A method for evaluating an effect of addition of an additive on a paper pulp furnish to predict the effect of addition of the additive on the pulp on a paper line, the method comprising the steps of:
placing the furnish in a holding container;
combining an additive with the furnish in the holding container;
forming a mixture of the furnish and additive by mixing the additive with the furnish with a mixing blade in the holding container under conditions that mimic the kinetic conditions with which the additive is mixed with the furnish on the paper line but that prolong a reaction between the additive and furnish such that the reaction requires longer to complete in the container than on the paper line;
transferring a portion of the furnish, without further mixing the furnish, through transfer lines to an intermediate container that maintains a constant hydrostatic head on the furnish in the intermediate container;
transferring at intervals an equal volume sample of the furnish from the intermediate container to a test container, without further mixing the furnish, and dewatering each said furnish sample in the test container to form a plurality of sheets each said sheet made from a separate equal volume sample of the furnish, wherein each said sheet is formed by subjecting each said equal volume sample of the furnish to a pressure differential created by providing a reduced pressure beneath the test container screen; and
determining one or more of properties of each said sheet, and determining the time elapsed from combining the additive with the furnish wherein the one or more properties of said sheet is chosen from the group consisting of pigment retention, fines retention, drainage time and visual appearance.

14. The method of claim 13 further comprising the step of sensing changes in the optical reflectance of the sheet by recording, simultaneously with beginning dewatering the sample, a pressure differential across the sample as a function of time throughout a period when water is being removed from said sample in the test container, determining points of inflection on a plot of the pressure differential versus time, and relating said points of inflection to drainage characteristics of a pulp furnish on a paper machine forming wire.

15. A drainage tester for evaluating a reaction in a paper pulp furnish to predict drainage time of the pulp on a paper machine, the tester comprising:
a holding container for the furnish;
a mixer for mixing an additive with the furnish in the holding container;
a test container having a screen bottom that separates furnish solid from slurry water;
transfer means for transferring at intervals a sample of the furnish through a transfer line from the holding container to an intermediate container, wherein the intermediate container maintains a constant hydrostatic head on the furnish;
separate means apart from the intermediate container for transferring a series of equal volume samples of the furnish from the intermediate container to the test container without mixing the furnish;
sheet forming means for forming a sheet from each said equal volume sample of the furnish; and
sensing means for automatically determining the drainage time of each said sample.

16. The device of claim 15 wherein the mixer comprises a horizontally rotating mixing blade that directs a portion of the furnish upward while the blade rotates.

17. The device of claim 15 further comprising peristaltic pumps in the transfer lines.

18. The device of claim 15 wherein the sensor detects changes in the optical characteristics of the sheet, beginning with dewatering the sample, and records the pressure differential across the sample as a function of time throughout the entire period when water is being removed, particularly recording a first point of inflection where pressure differential decreases as air first begins to be drawn through the sheet on the screen, a second point of inflection marking the point at which sheet compression in response to the pressure differential effectively ends, and a third point of inflection marking the point where water is no longer being removed, but air continues to be drawn through the sheet, and relating said recorded points of inflection to drainage characteristics of a pulp furnish on a paper machine forming wire.

19. A drainage tester for evaluating a reaction in a paper pulp furnish, the tester comprising:
a holding container for the furnish;
a mixer having a mixing mechanism that mixes additives with furnish in the holding container;
a test container having a screen bottom for separating furnish solids from slurry water;
an intermediate container that maintains a constant head on furnish in the intermediate container;
transfer lines that convey furnish between the holding container and the intermediate container, and between the intermediate and test container without substantial mixing of the furnish;
a suction generator that dewaters a furnish sample in the test container to form a sheet by subjecting the furnish to a pressure differential created by providing a reduced pressure beneath the test container screen bottom;
a timer that measures the time elapsed from mixing the additives with the furnish; and a sensor that detects changes in reflectance of the sheet and determines the drainage time.

20. The device of claim 19 wherein the mixing blade comprises a blade with a horizontal portion and a pair of oppositely inclined faces.

21. The device of claim 19 further comprising a peristaltic pump that transfers the furnish through the transfer lines.

22. A drainage tester for evaluating a reaction in a paper pulp furnish, the tester comprising:

a holding container for the furnish;

a mixer having a mixing mechanism that mixes additives with furnish in the holding container to form a mixture;

a test container having a screen bottom for separating furnish solids from slurry water;

an intermediate container that maintains a constant head on the mixture in the intermediate container by maintaining a constant depth of the mixture in the intermediate container;

transfer conduits for transferring the mixture from the holding container to the intermediate container, and from the intermediate container to the test container;

a suction generator that dewaters a furnish sample in the test container to form a sheet by subjecting the furnish to a pressure differential created by providing a reduced pressure beneath the test container screen bottom;

a timer that measures the time elapsed from mixing the additives with the furnish; and a sensor that detects changes in reflectance of the sheet and determines the drainage time.

\* \* \* \* \*